(12) United States Patent
Wright et al.

(10) Patent No.: US 9,308,171 B2
(45) Date of Patent: *Apr. 12, 2016

(54) PHARMACEUTICAL FORMULATION CONTAINING GELLING AGENT

(71) Applicant: Purdue Pharma L.P., Stamford, CT (US)

(72) Inventors: Curtis Wright, Rockport, MA (US); Benjamin Oshlack, Boca Raton, FL (US); Christopher Breder, Greenwich, CT (US)

(73) Assignees: Purdue Pharma L.P., Stamford, CT (US); The P.F. Laboratories, Inc., Totowa, NJ (US); Purdue Pharmaceuticals L.P., Wilson, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/610,156

(22) Filed: Jan. 30, 2015

(65) Prior Publication Data

US 2015/0148319 A1 May 28, 2015

Related U.S. Application Data

(63) Continuation of application No. 13/765,368, filed on Feb. 12, 2013, now Pat. No. 9,040,084, which is a continuation of application No. 12/262,015, filed on Oct. 30, 2008, now Pat. No. 8,389,007, which is a continuation of application No. 10/214,412, filed on Aug. 6, 2002, now abandoned.

(60) Provisional application No. 60/310,534, filed on Aug. 6, 2001.

(51) Int. Cl.
| | |
|---|---|
| A61K 47/38 | (2006.01) |
| A61K 45/06 | (2006.01) |
| A61K 47/08 | (2006.01) |
| A61K 31/485 | (2006.01) |
| A61K 47/36 | (2006.01) |
| A61K 9/16 | (2006.01) |
| A61K 9/20 | (2006.01) |
| A61K 9/00 | (2006.01) |
| A61K 31/439 | (2006.01) |
| A61K 47/10 | (2006.01) |
| A61K 31/167 | (2006.01) |
| A61K 31/192 | (2006.01) |
| A61K 47/26 | (2006.01) |
| A61K 31/48 | (2006.01) |
| A61K 9/48 | (2006.01) |
| A61K 9/50 | (2006.01) |
| A61K 47/32 | (2006.01) |
| A61K 9/08 | (2006.01) |
| A61K 9/28 | (2006.01) |
| A61K 47/12 | (2006.01) |
| A61K 47/34 | (2006.01) |
| A61K 9/06 | (2006.01) |
| A61K 31/4458 | (2006.01) |

(52) U.S. Cl.
CPC ............. *A61K 9/1641* (2013.01); *A61K 9/0002* (2013.01); *A61K 9/006* (2013.01); *A61K 9/0053* (2013.01); *A61K 9/06* (2013.01); *A61K 9/08* (2013.01); *A61K 9/1635* (2013.01); *A61K 9/1652* (2013.01); *A61K 9/205* (2013.01); *A61K 9/2013* (2013.01); *A61K 9/2031* (2013.01); *A61K 9/2054* (2013.01); *A61K 9/28* (2013.01); *A61K 9/284* (2013.01); *A61K 9/2806* (2013.01); *A61K 9/2846* (2013.01); *A61K 9/2866* (2013.01); *A61K 9/4808* (2013.01); *A61K 9/4858* (2013.01); *A61K 9/4866* (2013.01); *A61K 9/4891* (2013.01); *A61K 9/5078* (2013.01); *A61K 31/167* (2013.01); *A61K 31/192* (2013.01); *A61K 31/439* (2013.01); *A61K 31/4458* (2013.01); *A61K 31/48* (2013.01); *A61K 31/485* (2013.01); *A61K 45/06* (2013.01); *A61K 47/08* (2013.01); *A61K 47/10* (2013.01); *A61K 47/12* (2013.01); *A61K 47/26* (2013.01); *A61K 47/32* (2013.01); *A61K 47/34* (2013.01); *A61K 47/36* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 3,065,143 | A | 11/1962 | Christenson et al. |
| 3,133,132 | A | 5/1964 | Loeb et al. |

(Continued)

FOREIGN PATENT DOCUMENTS

| | | |
|---|---|---|
| EP | 0318262 A1 | 5/1989 |
| EP | 0661045 | 7/1995 |

(Continued)

OTHER PUBLICATIONS

Paragraph IV Patent Certification Notice for ANDA 202434 (2011).

(Continued)

*Primary Examiner* — Robert A Wax
*Assistant Examiner* — Randeep Singh
(74) *Attorney, Agent, or Firm* — Lowenstein Sandler LLP

(57) ABSTRACT

Disclosed in certain embodiments is a controlled release oral dosage form comprising a therapeutically effective amount of a drug susceptible to abuse together with one or more pharmaceutically acceptable excipients; the dosage form further including a gelling agent in an effective amount to impart a viscosity unsuitable for administration selected from the group consisting of parenteral and nasal administration to a solubilized mixture formed when the dosage form is crushed and mixed with from about 0.5 to about 10 ml of an aqueous liquid; the dosage form providing a therapeutic effect for at least about 12 hours when orally administered to a human patient.

24 Claims, No Drawings

(56) References Cited

U.S. PATENT DOCUMENTS

| | | | |
|---|---|---|---|
| 3,173,876 A | 3/1965 | Zobrist et al. | |
| 3,260,846 A | 7/1966 | Paulsen et al. | |
| 3,276,586 A | 10/1966 | Rosaen | |
| 3,541,005 A | 11/1970 | Strathmann et al. | |
| 3,541,006 A | 11/1970 | Bixler et al. | |
| 3,546,876 A | 12/1970 | Fokker et al. | |
| 3,845,770 A | 11/1974 | Theeuwes et al. | |
| 3,879,555 A | 4/1975 | Pachter et al. | |
| 3,916,889 A | 11/1975 | Russell | |
| 3,965,256 A | 6/1976 | Leslie | |
| 3,980,766 A * | 9/1976 | Shaw et al. | 514/648 |
| 4,063,064 A | 12/1977 | Saunders et al. | |
| 4,070,494 A * | 1/1978 | Hoffmeister et al. | 514/318 |
| 4,088,864 A | 5/1978 | Theeuwes et al. | |
| 4,160,020 A | 7/1979 | Ayer et al. | |
| 4,175,119 A | 11/1979 | Porter | |
| 4,200,098 A | 4/1980 | Ayer et al. | |
| 4,235,870 A | 11/1980 | Leslie | |
| 4,285,987 A | 8/1981 | Ayer et al. | |
| 4,293,539 A | 10/1981 | Ludwig et al. | |
| 4,366,310 A | 12/1982 | Leslie | |
| 4,385,057 A | 5/1983 | Bjork et al. | |
| 4,389,393 A | 6/1983 | Schor et al. | |
| 4,424,205 A | 1/1984 | LaHann et al. | |
| 4,443,428 A | 4/1984 | Oshlack et al. | |
| 4,457,933 A | 7/1984 | Gordon et al. | |
| 4,459,278 A | 7/1984 | Porter | |
| 4,588,580 A | 5/1986 | Gale et al. | |
| 4,599,342 A | 7/1986 | LaHann | |
| 4,610,870 A | 9/1986 | Jain et al. | |
| 4,612,008 A | 9/1986 | Wong et al. | |
| 4,629,623 A | 12/1986 | Balazs et al. | |
| 4,666,705 A | 5/1987 | DeCrosta et al. | |
| 4,764,378 A | 8/1988 | Keith et al. | |
| 4,765,989 A | 8/1988 | Wong et al. | |
| 4,769,372 A | 9/1988 | Kreek | |
| 4,785,000 A | 11/1988 | Kreek et al. | |
| 4,806,341 A | 2/1989 | Chien et al. | |
| 4,812,446 A | 3/1989 | Brand | |
| 4,834,984 A | 5/1989 | Goldie et al. | |
| 4,844,909 A | 7/1989 | Goldie et al. | |
| 4,861,598 A | 8/1989 | Oshlack | |
| 4,957,681 A | 9/1990 | Klimesch et al. | |
| 4,970,075 A | 11/1990 | Oshlack | |
| 4,990,341 A | 2/1991 | Goldie et al. | |
| 4,992,277 A | 2/1991 | Sangekar et al. | |
| 5,026,556 A | 6/1991 | Drust et al. | |
| 5,059,600 A | 10/1991 | Gawin et al. | |
| 5,069,909 A | 12/1991 | Sharma et al. | |
| 5,111,942 A | 5/1992 | Bernardin | |
| 5,113,585 A | 5/1992 | Rogers et al. | |
| 5,114,942 A | 5/1992 | Gawin et al. | |
| 5,130,311 A | 7/1992 | Guillaumet et al. | |
| 5,149,538 A | 9/1992 | Granger et al. | |
| 5,169,645 A | 12/1992 | Shukla et al. | |
| 5,202,128 A | 4/1993 | Morella et al. | |
| 5,215,758 A | 6/1993 | Krishnamurthy | |
| 5,225,199 A | 7/1993 | Hidaka et al. | |
| 5,232,685 A | 8/1993 | Speck et al. | |
| 5,232,934 A | 8/1993 | Downs | |
| 5,240,711 A | 8/1993 | Hille et al. | |
| 5,266,331 A | 11/1993 | Oshlack et al. | |
| 5,273,758 A | 12/1993 | Royce | |
| 5,273,760 A | 12/1993 | Oshlack et al. | |
| 5,286,493 A | 2/1994 | Oshlack et al. | |
| 5,290,816 A | 3/1994 | Blumberg | |
| 5,300,302 A | 4/1994 | Tachon et al. | |
| 5,321,012 A | 6/1994 | Mayer et al. | |
| 5,324,351 A | 6/1994 | Oshlack et al. | |
| 5,330,766 A | 7/1994 | Morella et al. | |
| 5,356,467 A | 10/1994 | Oshlack et al. | |
| 5,368,852 A | 11/1994 | Umemoto et al. | |
| 5,376,705 A | 12/1994 | Leys et al. | |
| 5,378,474 A | 1/1995 | Morella et al. | |
| 5,399,351 A | 3/1995 | Leschiner et al. | |
| 5,403,868 A | 4/1995 | Reid et al. | |
| 5,409,944 A | 4/1995 | Black et al. | |
| 5,411,745 A | 5/1995 | Oshlack et al. | |
| 5,422,123 A | 6/1995 | Conte et al. | |
| 5,436,265 A | 7/1995 | Black et al. | |
| 5,472,712 A | 12/1995 | Oshlack et al. | |
| 5,472,943 A | 12/1995 | Crain et al. | |
| 5,474,995 A | 12/1995 | Ducharme et al. | |
| 5,478,577 A | 12/1995 | Sackler et al. | |
| 5,500,227 A | 3/1996 | Oshlack et al. | |
| 5,502,058 A | 3/1996 | Mayer et al. | |
| 5,505,959 A | 4/1996 | Tachon et al. | |
| 5,508,042 A | 4/1996 | Oshlack et al. | |
| 5,508,043 A | 4/1996 | Krishnamurthy | |
| 5,510,368 A | 4/1996 | Lau et al. | |
| 5,514,680 A | 5/1996 | Weber et al. | |
| 5,521,213 A | 5/1996 | Prasit et al. | |
| 5,536,752 A | 7/1996 | Ducharme et al. | |
| 5,549,912 A | 8/1996 | Oshlack et al. | |
| 5,550,142 A | 8/1996 | Ducharme et al. | |
| 5,552,422 A | 9/1996 | Gauthier et al. | |
| 5,556,838 A | 9/1996 | Mayer et al. | |
| 5,580,578 A | 12/1996 | Oshlack et al. | |
| 5,593,695 A | 1/1997 | Merrill et al. | |
| 5,593,994 A | 1/1997 | Batt et al. | |
| 5,604,253 A | 2/1997 | Lau et al. | |
| 5,604,260 A | 2/1997 | Guay et al. | |
| 5,616,601 A | 4/1997 | Khanna et al. | |
| 5,639,476 A | 6/1997 | Oshlack et al. | |
| 5,639,780 A | 6/1997 | Lau et al. | |
| 5,656,295 A | 8/1997 | Oshlack et al. | |
| 5,667,805 A | 9/1997 | Merrill et al. | |
| 5,672,360 A | 9/1997 | Sackler et al. | |
| 5,679,650 A | 10/1997 | Fukunaga et al. | |
| 5,681,585 A | 10/1997 | Oshlack et al. | |
| 5,695,781 A | 12/1997 | Zhang et al. | |
| 5,702,725 A | 12/1997 | Merrill et al. | |
| 5,730,716 A | 3/1998 | Beck et al. | |
| 5,741,524 A | 4/1998 | Staniforth et al. | |
| 5,762,963 A | 6/1998 | Byas-Smith | |
| 5,766,623 A * | 6/1998 | Ayres et al. | 424/441 |
| 5,811,126 A | 9/1998 | Krishnamurthy | |
| 5,843,480 A | 12/1998 | Miller et al. | |
| 5,849,240 A | 12/1998 | Miller et al. | |
| 5,866,164 A | 2/1999 | Kuczynski et al. | |
| 5,879,705 A | 3/1999 | Heafield et al. | |
| 5,891,471 A | 4/1999 | Miller et al. | |
| 5,891,919 A | 4/1999 | Blum et al. | |
| 5,914,131 A | 6/1999 | Merrill et al. | |
| 5,948,787 A | 9/1999 | Merrill et al. | |
| 5,958,452 A | 9/1999 | Oshlack et al. | |
| 5,958,459 A | 9/1999 | Chasin et al. | |
| 5,965,161 A | 10/1999 | Oshlack et al. | |
| 5,965,163 A | 10/1999 | Miller et al. | |
| 5,968,551 A | 10/1999 | Oshlack et al. | |
| 6,024,982 A | 2/2000 | Oshlack et al. | |
| 6,103,261 A | 8/2000 | Chasin et al. | |
| 6,120,751 A | 9/2000 | Unger | |
| 6,124,282 A | 9/2000 | Sellers et al. | |
| 6,126,969 A | 10/2000 | Shah et al. | |
| 6,136,864 A | 10/2000 | Nichols et al. | |
| 6,143,322 A | 11/2000 | Sackler et al. | |
| 6,153,621 A | 11/2000 | Hamann | |
| 6,162,467 A | 12/2000 | Miller et al. | |
| 6,210,712 B1 | 4/2001 | Edgren et al. | |
| 6,210,714 B1 | 4/2001 | Oshlack et al. | |
| 6,223,075 B1 | 4/2001 | Beck et al. | |
| 6,228,863 B1 | 5/2001 | Palermo et al. | |
| 6,245,357 B1 | 6/2001 | Edgren et al. | |
| 6,251,430 B1 | 6/2001 | Zhang et al. | |
| 6,277,398 B1 | 8/2001 | Caruso | |
| 6,294,194 B1 | 9/2001 | Horhota et al. | |
| 6,309,668 B1 | 10/2001 | Bastin et al. | |
| 6,348,469 B1 | 2/2002 | Seth | |
| 6,352,721 B1 | 3/2002 | Faour | |
| 6,375,957 B1 | 4/2002 | Kaiko et al. | |
| 6,403,056 B1 | 6/2002 | Unger | |
| 6,419,954 B1 | 7/2002 | Chu | |
| 6,436,441 B1 | 8/2002 | Sako et al. | |

(56) References Cited

U.S. PATENT DOCUMENTS

| | | |
|---|---|---|
| 6,440,464 B1 | 8/2002 | Hsia et al. |
| 6,488,963 B1 | 12/2002 | McGinity |
| 6,491,949 B2 | 12/2002 | Faour et al. |
| 6,559,159 B2 | 5/2003 | Carroll et al. |
| 6,572,885 B2 | 6/2003 | Oshlack et al. |
| 6,593,367 B1 | 7/2003 | Dewey et al. |
| 6,627,635 B2 | 9/2003 | Palermo et al. |
| 6,696,088 B2 | 2/2004 | Oshlack et al. |
| 6,733,783 B2 | 5/2004 | Oshlack et al. |
| 6,808,720 B2 | 10/2004 | Unger |
| 6,995,169 B2 | 2/2006 | Chapleo et al. |
| 7,141,250 B2 | 11/2006 | Oshlack et al. |
| 7,144,587 B2 | 12/2006 | Oshlack et al. |
| 7,157,103 B2 | 1/2007 | Sackler |
| 7,201,920 B2 | 4/2007 | Kumar et al. |
| 7,276,250 B2 | 10/2007 | Baichwal et al. |
| 7,332,182 B2 | 2/2008 | Sackler |
| 7,510,726 B2 | 3/2009 | Kumar et al. |
| 7,727,557 B2 | 6/2010 | Sackler |
| 7,776,314 B2 | 8/2010 | Bartholomaus |
| 7,842,307 B2 | 11/2010 | Oshlack et al. |
| 7,943,174 B2 | 5/2011 | Oshlack et al. |
| 7,981,439 B2 | 7/2011 | Kumar et al. |
| 8,017,148 B2 | 9/2011 | Sackler |
| 8,075,872 B2 | 12/2011 | Arkenau-Maric |
| 8,101,630 B2 | 1/2012 | Kumar et al. |
| 8,114,383 B2 | 2/2012 | Barthalomaus |
| 8,114,384 B2 | 2/2012 | Arkenau |
| 8,192,722 B2 | 6/2012 | Arkenau-Maric |
| 8,309,060 B2 | 11/2012 | Bartholomaus et al. |
| 8,337,888 B2 | 12/2012 | Wright et al. |
| 8,389,007 B2 | 3/2013 | Wright et al. |
| 8,409,616 B2 | 4/2013 | Kumar et al. |
| 8,524,275 B2 | 9/2013 | Oshlack et al. |
| 8,529,948 B1 | 9/2013 | Wright et al. |
| 8,609,683 B2 | 12/2013 | Wright et al. |
| 8,637,540 B2 | 1/2014 | Kumar et al. |
| 8,652,497 B2 | 2/2014 | Sackler |
| 8,652,515 B2 | 2/2014 | Sackler |
| 8,871,265 B2 | 10/2014 | Wright et al. |
| 8,999,961 B2 | 4/2015 | Wright et al. |
| 9,034,376 B2 | 5/2015 | Wright et al. |
| 9,040,084 B2 | 5/2015 | Wright et al. |
| 9,044,435 B2 | 6/2015 | Wright et al. |
| 9,060,976 B2 | 6/2015 | Wright et al. |
| 2002/0187192 A1 | 12/2002 | Joshi et al. |
| 2003/0004177 A1 | 1/2003 | Kao et al. |
| 2003/0021841 A1 | 1/2003 | Matharu et al. |
| 2003/0026838 A1 | 2/2003 | Farrell |
| 2003/0035839 A1 | 2/2003 | Hirsh et al. |
| 2003/0054027 A1 | 3/2003 | Unger |
| 2003/0059471 A1 | 3/2003 | Compton et al. |
| 2003/0064099 A1 | 4/2003 | Oshlack et al. |
| 2003/0064122 A1 | 4/2003 | Goldberg et al. |
| 2003/0068276 A1 | 4/2003 | Hughes et al. |
| 2003/0068370 A1 | 4/2003 | Sackler |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0082230 A1 | 5/2003 | Baichwal et al. |
| 2003/0124061 A1 | 7/2003 | Roberts |
| 2003/0124185 A1 | 7/2003 | Oshlack et al. |
| 2003/0125347 A1 | 7/2003 | Anderson et al. |
| 2003/0126428 A1 | 7/2003 | Liu et al. |
| 2003/0170181 A1 | 9/2003 | Midha |
| 2003/0232081 A1 | 12/2003 | Doshi et al. |
| 2004/0047907 A1 | 3/2004 | Oshlack et al. |
| 2004/0126428 A1 | 7/2004 | Hughes et al. |
| 2004/0131552 A1 | 7/2004 | Oehm |
| 2004/0151791 A1 | 8/2004 | Mayo-Alvarez et al. |
| 2004/0224020 A1 | 11/2004 | Schoenhard |
| 2004/0228802 A1 | 11/2004 | Chang et al. |
| 2004/0241234 A1 | 12/2004 | Vilkov |
| 2004/0253310 A1 | 12/2004 | Fischer et al. |
| 2004/0266807 A1 | 12/2004 | Oshlack et al. |
| 2005/0020613 A1 | 1/2005 | Boehm et al. |
| 2005/0031546 A1 | 2/2005 | Bartholomaus et al. |
| 2005/0063909 A1 | 3/2005 | Wright et al. |
| 2005/0106249 A1 | 5/2005 | Hwang et al. |
| 2005/0112067 A1 | 5/2005 | Kumar et al. |
| 2005/0112201 A1 | 5/2005 | Baichwal et al. |
| 2005/0118267 A1 | 6/2005 | Baichwal et al. |
| 2005/0158382 A1 | 7/2005 | Cruz et al. |
| 2005/0163717 A1 | 7/2005 | Anderson et al. |
| 2005/0186139 A1 | 8/2005 | Bartholomaus |
| 2005/0214223 A1 | 9/2005 | Bartholomaeus et al. |
| 2005/0236741 A1 | 10/2005 | Arkenau |
| 2005/0276853 A1 | 12/2005 | Baichwal et al. |
| 2006/0002860 A1 | 1/2006 | Bartholomaus |
| 2006/0018837 A1 | 1/2006 | Preston et al. |
| 2006/0039864 A1 | 2/2006 | Bartholomaus |
| 2006/0165790 A1 | 7/2006 | Walden et al. |
| 2006/0188447 A1 | 8/2006 | Arkenau-Maric |
| 2006/0193782 A1 | 8/2006 | Bartholomaus |
| 2006/0251721 A1 | 11/2006 | Cruz et al. |
| 2007/0003616 A1 | 1/2007 | Arkenau-Maric |
| 2007/0003617 A1 | 1/2007 | Fischer et al. |
| 2007/0110807 A1 | 5/2007 | Vergnault et al. |
| 2007/0166234 A1 | 7/2007 | Kumar et al. |
| 2007/0264327 A1 | 11/2007 | Kumar et al. |
| 2008/0063725 A1 | 3/2008 | Guimberteau et al. |
| 2008/0095843 A1 | 4/2008 | Nutalapati et al. |
| 2008/0176955 A1 | 7/2008 | Heck et al. |
| 2008/0254123 A1 | 10/2008 | Fischer et al. |
| 2008/0260815 A1 | 10/2008 | Hayes et al. |
| 2009/0081290 A1 | 3/2009 | McKenna et al. |
| 2009/0169587 A1 | 7/2009 | Baichwal et al. |
| 2009/0215808 A1 | 8/2009 | Yum et al. |
| 2010/0221293 A1 | 9/2010 | Cruz et al. |
| 2011/0262532 A1 | 10/2011 | Oshlack et al. |
| 2012/0164220 A1 | 6/2012 | Huang |
| 2013/0245055 A1 | 9/2013 | Wright et al. |
| 2014/0213606 A1 | 7/2014 | Wright et al. |
| 2014/0371257 A1 | 12/2014 | Wright et al. |
| 2015/0005331 A1 | 1/2015 | Wright et al. |
| 2015/0031718 A1 | 1/2015 | Wright et al. |
| 2015/0140083 A1 | 5/2015 | Wright et al. |
| 2015/0147391 A1 | 5/2015 | Wright et al. |
| 2015/0148319 A1 | 5/2015 | Wright et al. |
| 2015/0182628 A1 | 7/2015 | Wright et al. |

FOREIGN PATENT DOCUMENTS

| | | |
|---|---|---|
| EP | 698389 | 2/1996 |
| EP | 1293195 A1 | 3/2003 |
| WO | 91/07950 | 6/1991 |
| WO | 9310765 | 5/1993 |
| WO | 91/20947 | 8/1995 |
| WO | WO-95/20947 A1 | 8/1995 |
| WO | 97/12605 | 4/1997 |
| WO | 97/37689 | 10/1997 |
| WO | 97/48385 | 12/1997 |
| WO | 97/49384 | 12/1997 |
| WO | 99/20255 | 4/1999 |
| WO | 99/32120 | 7/1999 |
| WO | WO-99/32119 A1 | 7/1999 |
| WO | 99/44591 | 9/1999 |
| WO | 0033835 | 6/2000 |
| WO | WO-01/58447 A1 | 8/2001 |
| WO | 02/087558 | 11/2002 |
| WO | WO-02/094254 A2 | 11/2002 |
| WO | WO-03/015531 A2 | 2/2003 |
| WO | 03024430 | 3/2003 |
| WO | WO-03/026743 A2 | 4/2003 |
| WO | 03035020 | 5/2003 |
| WO | WO-03/092676 A1 | 11/2003 |
| WO | WO-2004/026256 A2 | 1/2004 |
| WO | WO-2004/026283 A1 | 4/2004 |

(56) References Cited

FOREIGN PATENT DOCUMENTS

| WO | WO-2004/037259 A1 | 5/2004 |
|---|---|---|
| WO | WO-2005/053587 A1 | 6/2005 |
| WO | 20100078486 | 7/2010 |

OTHER PUBLICATIONS

Paragraph IV Patent Certification Notice for ANDA 203235 (2011).
Paragraph IV Patent Certification Notice for ANDA 202372 (2011).
Paragraph IV Patent Certification Notice for ANDA 202483 (2011).
Paragraph IV Patent Certification Notice for ANDA 202762 (2011).
Paragraph IV Patent Certification Notice for Amendment to ANDA 202762 (2011).
Paragraph IV Patent Certification Notice for ANDA 202455 (2011).
Paragraph IV Patent Certification Notice for ANDA 202352 (2011).
Woodburn, K.R., et al., "Vascular Complications of Injecting Drug Misuse", British Journal of Surgery, 1996, vol. 83, p. 1329-1334.
Kim, C., "Drug Release from Compressed Hydrophilic POLYOX-WSR Tablets", Journal of Pharmaceutical Sciences, vol. 84, No. 3, Mar. 1995, p. 303-306.
Apicella, A., "Poly(ethylene oxide) (PEO) and Different Molecular Weight PEO Blends Monolithic Devices for Drug Release", Biomateriais, vol. 14, No. 2, 1993, p. 83-90.
Deighan, C.J., et al., "Rhabdomyolysis and Acute Renal Failure Resulting From Alcohol and Drug Abuse", QJ Med, Vol, 93, 2000, p. 29-33.
Kalant, H., et al,, "Death in Amphetamine Users: Causes and Rates", CMA Journal, vol. 112, Feb. 8, 1975, p. 299-304.
U.S. Pharmacopeia, p. 2206, 1995.
Paragraph IV Patent Certification Notice for ANDA 202352 (2013).
Paragraph IV Patent Certification Notice for ANDA 202372 (2013).
Paragraph IV Patent Certification for ANDA 202434 (2013).
Paragraph IV Patent Certification Notice for ANDA 202483 (2013).
Paragraph IV Patent Certification Notice for ANDA 203235 (2013).
Ortho-McNeil-Janssen Pharmaceuticals, Inc. (2010). Prescribing information for Concerta Extended-Release Tablets.
Written Opinion and International Search Report for International Patent Application No. PCT/IB2011/003152 issed Sep. 19, 2012.
U.S. Appl. No. 13/333,560—Non-Final Rejection dated Jan. 29, 2013.
U.S. Appl. No. 13/333,560—Amendment/Response dated Apr. 29, 2013.
Complaint 1:13-cv-01272-SHS (Feb. 25, 2013).
Answer and Counterclaims 1:13-cv-01272-SHS (Mar. 8, 2013).
Answer Consent to Counterclaims 1:13-cv-01272-SHS (Apr. 1, 2013).
Consent Judgement :13-cv-01272-SHS (May 1, 2013).
Complaint 1:13-cv-03188-SHS (May 10, 2013).
Answer; Affirmative Defenses and Counterclaims 1:13-cv-03188-SHS (Jun. 7, 2013).
Complaint 1:13-cv-03374-SHS (May 17, 2013).
Answer and Counterclaims 1:13-cv-03374-SHS (Jun. 3, 2013).
Complaint 1:13-cv-03372-SHS (May 17, 2013).
Moroni, et al., "Application of Polyoxyethylene) Homopolymers in Sustained Release Solid Formulations", Drug Dev, and Indus. Pharmacy, 21(12), 1411-28 (1995).
Apicella, et al., "Poly(ethylene oxide) (PEO) Constant Release and Pharmaceutical Applications, Chapter 3 (1992) Monolithic Devices," Polymers in Medicine: Biomedical and Pharmaceutical Applications, Chapter 3 (1992).
Apicella, et al., "Poly(ethylene oxide)-Based Delivery Systems", Polymeric Drugs and Drug Administration, ACS Symposium Series 545, Chapter 9 (1994).
Zhang, F, et at, "Properties of Sustained-Release Tablets Prepared by Hot-Melt Extrusion", Pharmaceutical Development and Technology, vol. 4, No. 2, p. 241-250 (1999).
Maggi, L., et al., "Dissolution Behaviour of Hydrophilic Matrix Tablets Containing Two Different Polyethylene Oxides (PEOs) for the Controlled Release of a Water-Soluble Drug", Biomaterials, vol. 23, p. 1113-1119 (2002).
The 1997 Physician's Desk Reference ("PDR") entry for Oxycontin®.
Paragraph IV Patent Certification Notice for ANDA 202455 (2013).
Complaint 1:13-cv-04606 (Jul. 2, 2013).
Yang, et al., "Characterization of Compressibility and Compactibility of Poiy(ethylene oxide) Polymers for Modified Release Apptcation by Compaction Simulator", Journal of Pharmaceutical Sciences, vol. 85, No. 10, Oct. 1996.
Wilkins, Jeffrey, N., "Pharmacotherapy of Schizophrenia Patients with Comorbid Substance Abuse", Schiizophrenia Bulletin, vol. 23, No. 2, 1997, http://schizophreniabulletin.oxfordjournals.org.
Paragraph IV Patent Certification Notice for ANDA 203915 (2013).
Findings of Fact and Conclusions of Law, in re: Oxycontin Antitrust Litigation, Case 1:04-md-01603-SHS, Jan. 14, 2014.
Opinion & Order filed May 27, 2014, Case 1:04-md-01603-SHS, 24 pgs.
Declaration of Interference No. 106,004 filed Apr. 22, 2014, 8 pgs.
Bettini et al., "Translocation of drug particles in HPMC matrix gel layer: effect of drug solubility and influence on release rate," Journal of Controlled Release, vol. 70, No. 3, Feb. 2001, pp. 383-391.
Barker, N., "Kinetics of thermal gelation of methylcellulose and hydroxypropylmethylcellulose in aqueous solutions," Carbohydrate Polymers, vol. 26, No. 3, Jan. 1995, pp. 195-203.
USPTO Final Rejection for U.S. Appl. No. 13/890,874, dated Mar. 11, 2014.
USPTO Response for U.S. Appl. No. 13/690,874, dated Jun. 10, 2014.
USPTO Response for U.S. Appl. No. 13/890,874, dated Oct. 14, 2014.
USPTO Final Rejection for U.S. Appl. No. 13/946,418, dated Apr. 10, 2014.
USPTO Response for U.S. Appl. No. 13/946,418, dated Jun. 10, 2014.
USPTO Response for U.S. Appl. No. 13/946,418, dated Oct. 14, 2014.
USPTO Non-Final Rejection for U.S. Appl. No. 14/243,580, dated Oct. 2, 2014.
USPTO Non-Final Rejection for U.S. Appl. No. 14/460,134, dated Oct. 2, 2014.
USPTO Non-Final Rejection for U.S. Appl. No. 14/460,170, dated Oct. 2, 2014.
USPTO Non-Final Rejection for U.S. Appl. No. 14/470,631, dated Oct. 21, 2014.
USPTO Non-Final Rejection for U.S. Appl. No. 14/470,662, dated Nov. 4, 2014.
USPTO Non-Final Rejection for U.S. Appl. No. 14/484,077, dated Oct. 22, 2014.
USPTO Non-Final Rejection for U.S. Appl. No. 13/890,874 dated Dec. 18, 2013.
USPTO Response for U.S. Appl. No. 13/890,874 dated Feb. 28, 2014.
USPTO Advisory Action for U.S. Appl. No. 13/890,874 dated Jun. 19, 2014.
USPTO Non-Final Rejection for U.S. Appl. No. 13/946,418 dated Sep. 12, 2013.
USPTO Response for U.S. Appl. No. 13/946,418 dated Dec. 12, 2013.
USPTO Advisory Action for U.S. Appl. No. 13/946,418 dated Jun. 23, 2014.
USPTO Response for U.S. Appl. No. 14/460,134 dated Jan. 2, 2015.
USPTO Response for U.S. Appl. No. 14/460,170 dated Jan. 2, 2015.
Sarkar, N., "Thermal Gelation Properties of Methyl and Hydroxypropyl Methylocellulose," Journal of Applied Polymer Science, vol. 24, No. 4, Aug. 1979, pp. 1073-1087.
Bhatia, R., "Effect of Molecular Mass, Concentration and Temperature on the Rheological Properties of Non-Newtonian Agueous Polymeric Solutions," 114, 2011, 202 pgs.
Kibbe, Arthur, H., "Polyethylene Oxide," Handbook of Pharmaceutical Excipients, Third Edition, 2000, pp. 399-400, PhP Pharmaceutical Press, London, United Kingdom.
Stafford, J.W., et al., "Temperature dependence of the disintegration times of compressed tablets containing hydroxypropylcellulose as binder," Journal of Pharmacy and Pharmacology, vol. 30, No. 1, Sep. 1978, pp. 1-5, John Wiley & Sons, New York, United States.

(56) References Cited

OTHER PUBLICATIONS

Ansel, Howard C., et al., Pharmaceutical Dosage Forms and Drug Delivery Systems, 7th Edition, 1999, pp. 1-2, 23-163, 179-243, 397-449, 552-562, Lippincott Williams & Wilkins, United States.

Aulton Michael E., et al., Pharmaceutics, The Science of Dosage Form Design, Reprinted 2000, pp. 1-2, 17-37, 62-80, 131-211, 304-321, 359-380, 550-677, Churchill Livingston, China.

Chien, Yie W., et al., "Syringeability of Nonaqueous Parenteral Formulations—Development and Evaluation of Testing Apparatus," Journal of Parenteral Science and Technology, vol. 35, No. 6, Nov. 1981, pp. 281-284.

Dexter, M.B., et al., "The Evaluation of the Force to Expel Oily Injection Vehicles from Syringes," J. Pharm. Pharmacol., vol. 31, Aug. 1979, The Pharmaceutical Society of Great Britain, pp. 497-500.

Gennaro, Alfonso, Remington: The Science and Practice of Pharmacy, 20th Edition, 2000, pp. 1-3, 335-355, 654-666, 669-752, 780-820, 858-929, 995-10004, 1098-1155, 1175-1182, 1395-1399, 2037-2038, Lippincott Williams & Wilkins, Baltimore, MD, United States.

Hardman, Joel G., et al., Goodman & Gilman's The Pharmacological Basis of Therapeutics, 9th Edition, 1996, pp. 3-27, 521-555, 557-577, McGraw-Hill, United States.

Hem, Stanley, et al., "Tissue Irritation Evaluation of Potential Parenteral Vehicles," Drug Development Communications, 1:5, 1974, pp. 471-477, Marcel Dekker, Inc.

Huang, H., et al., "Preparation of Controlled Release Oral Dosage Forms by Low Temperature Melt Extrusion," The AAPS Journal, AAPS PharmaSci, 2000, 2(S1), 3 pgs.

Heng, Paul, et al., "Role of Surfactant on Drug Release from Tablets", Drug Development and Industrial Pharmacy, Oct. 20, 2008, pp. 951-962, Taylor & Francis, London, United Kingdom.

Industrial and Engineering Chemistry I/EC, Golden Anniversary Year 50, Pattern for Progress, vol. 50, No. 1, Jan. 10, 1958, pp. 8-11, American Chemical Society, Easton, PA, United States.

Handbook of Pharmaceutical Excipients, 1986, pp. 234-239, American Pharmaceutical Association, Washington D.C., United States.

Meier, Barry, "U.S. Asks Painkiller Maker to Help Curb Wide Abuse," The New York Times, May 1, 2001, 3 pgs.

Modern Pharmaceutics, 3rd Edition, Drugs and the Pharmaceutical Sciences, vol. 72, 1996, pp. 21-73, 75-119, 121-153, 155-178, 333-394, 441-487, 575-609, 727-772, Marcel Dekker, Inc., United States.

Philip, George, et al., "The Human Nasal Response to Capsaicin," J. Allergy Clin. Immonul., vol. 94, No. 6, Part 1, Dec. 1994, pp. 1035-1045, Mosy-Year Book, Inc., Baltimore, MD, United States.

The 1997 Physician's Desk Reference ("PDR"), $51^{st}$ edition, Nov. 1996, pp. 955-957, 988-989, 2163-2167, 2366-2367, Medical Economics Company, Inc., Montvale, NJ, United States.

Tough, Paul, "The Alchemy of Oxycontin: From Pain Relief to Drug Addiction," The New York Times, Jul. 29, 2001, 14 pgs.

U.S. Pharmacopeia & National Formulary 24/19, The Standard of Quality, United States Pharmacopeial Convention, Inc., 1999, pp. 1233-1238, 1372-1375, 1941-1951, 2002-2003, 2442-2443, 2493-2498, National Publishing, Philadelphia, PA, United States.

Zhang, Feng, Dissertation: "Hot-Melt Extrusion as a Novel Technology to Prepare Sustained-Release Dosage Forms," The University of Texas at Austin, pp. v-xxv, 1-260, Dec. 1999, UMI Microform 9959618, Bell & Howell Information and Learning Company, Ann Arbor, MI, United States.

Findings of Fact and Conclusions of Law, In re: Oxycontin Antitrust Litigation, Case 1:04-md-01603-SHS, Apr. 8, 2015, pp. 1-69.

* cited by examiner

PHARMACEUTICAL FORMULATION CONTAINING GELLING AGENT

RELATED APPLICATIONS

This application is a continuation of U.S. patent application Ser. No. 13/765,368 filed Feb. 12, 2013, which is a continuation of U.S. patent application Ser. No. 12/262,015, filed Oct. 30, 2008 and issued as U.S. Pat. No. 8,389,007 on Mar. 5, 2013, which is a continuation of U.S. patent application Ser. No. 10/214,412, filed Aug. 6, 2002, which claims the benefit of U.S. Provisional Application No. 60/310,534, filed Aug. 6, 2001. The contents of these applications are hereby incorporated by reference in their entirety.

BACKGROUND OF THE INVENTION

Opioid analgesics are sometimes the subject of abuse. Typically, a particular dose of an opioid analgesic is more potent when administered parenterally as compared to the same dose administered orally. Therefore, one popular mode of abuse of oral opioid formulations involves the extraction of the opioid from the dosage form, and the subsequent injection of the opioid (using any "suitable" vehicle for injection) in order to achieve a "high." Also, some formulations can be tampered with in order to provide the opioid agonist contained therein better available for illicit use. For example, a controlled release opioid agonist formulation can be crushed in order to provide the opioid contained therein available for immediate release upon oral or nasal administration. An opioid formulation can also be abusable by administration of more than the prescribed dose of the drug.

Opioid antagonists have been combined with certain opioid agonists in order to deter the parenteral abuse of opioid agonists. In the prior art, the combination of immediate release pentazocine and naloxone has been utilized in tablets available in the United States, commercially available as Talwin® Nx from Sanofi-Winthrop. Talwin® Nx contains immediate release pentazocine hydrochloride equivalent to 50 mg base and naloxone hydrochloride equivalent to 0.5 mg base. A fixed combination therapy comprising tilidine (50 mg) and naloxone (4 mg) has been available in Germany for the management of pain since 1978 (Valoron®N, Goedecke). A fixed combination of buprenorphine and naloxone was introduced in 1991 in New Zealand (Temgesic® Nx, Reckitt & Colman) for the treatment of pain.

Purdue Pharma EP currently markets sustained-release oxycodone in dosage forms containing 10, 20, 40, and 80 mg oxycodone hydrochloride under the tradename OxyContin.

U.S. Pat. Nos. 5,266,331; 5,508,042; 5,549,912 and 5,656,295 disclose sustained release oxycodone formulations.

U.S. Pat. Nos. 4,769,372 and 4,785,000 to Kreek describe methods of treating patients suffering from chronic pain or chronic cough without provoking intestinal dysmotility by administering 1 to 2 dosage units comprising from about 1.5 to about 100 mg of opioid analgesic or antitussive and from about 1 to about 18 mg of an opioid antagonist having little to no systemic antagonist activity when administered orally, from 1 to 5 times daily.

U.S. Pat. No. 6,228,863 to Palermo et al. describes compositions and methods of preventing abuse of opioid dosage forms.

WO 99/32119 to Kaiko et al. describes compositions and methods of preventing abuse of opioid dosage forms.

U.S. Pat. No. 5,472,943 to Crain et al. describes methods of enhancing the analgesic potency of bimodally acting opioid agonists by administering the agonist with an opioid antagonist.

U.S. Pat. No. 3,980,766 to Shaw et al., is related to drugs which are suitable for therapy in the treatment of narcotic drug addiction by oral use, e.g., methadone, formulated to prevent injection abuse through concentration of the active component in aqueous solution by incorporating in a solid dosage or tablet form of such drug an ingestible solid having thickening properties which cause rapid increase in viscosity upon concentration of an aqueous solution thereof.

However, there still exists a need for a safe and effective treatment of pain with opioid analgesic dosage forms which are less subject to abuse than current therapies.

All documents cited herein, including the foregoing, art incorporated by reference in their entireties for all purposes.

OBJECTS AND SUMMARY OF THE INVENTION

It is an object of certain embodiments of the invention to provide an oral dosage form of an opioid analgesic which is subject to less parenteral abuse than other dosage forms.

It is an object of certain embodiments of the invention to provide an oral dosage form of an opioid analgesic which is subject to less intranasal abuse than other dosage forms.

It is an object of certain embodiments of the invention to provide an oral dosage form of an opioid analgesic which is subject to less oral abuse than other dosage forms.

It is a further object of certain embodiments of the invention to provide an oral dosage form of an opioid analgesic which is subject to less diversion than other dosage forms.

It is a further object of certain embodiments of the invention to provide a method of treating pain in human patients with an oral dosage form of an opioid analgesic while reducing the abuse potential of the dosage form.

It is a further object of certain embodiments of the invention to provide a method of manufacturing an oral dosage form of an opioid analgesic such that it has less abuse potential.

These objects and others are achieved by the present invention, which is directed in part to an oral dosage form comprising an opioid analgesic; and at least one aversive agent for reducing the abuse of the opioid analgesic.

In certain embodiments of the present invention, the oral dosage forms of the present invention comprising an opioid analgesic; and an aversive agent or agents as a component(s) of the dosage form helps to prevent injection, inhalation, and/or oral abuse by decreasing the "attractiveness" of the dosage form to a potential abuser.

In certain embodiments of the present invention, the dosage form comprises an aversive agent such as a bittering agent to discourage an abuser from tampering with the dosage form and thereafter inhaling or swallowing the tampered dosage form. Preferably, the bittering agent is released when the dosage form is tampered with and provides an unpleasant taste to the abuser upon inhalation and/or swallowing of the tampered dosage form.

In certain embodiments of the present invention, the dosage form comprises an aversive agent such as an irritant to discourage an abuser from tampering with the dosage form and thereafter inhaling, injecting, or swallowing the tampered dosage form. Preferably, the irritant is released when the dosage form is tampered with and provides a burning or irritating effect to the abuser upon inhalation, injection, and/or swallowing of the tampered dosage form.

In certain embodiments of the present invention, the dosage form comprises an aversive agent such as a gelling agent to discourage an abuser from tampering with the dosage form and thereafter inhaling, injecting, and/or swallowing the tampered dosage form. Preferably, the gelling agent is released when the dosage form is tampered with and provides a gel-like quality to the tampered dosage form which slows the absorption of the opioid analgesic such that an abuser is less likely to obtain a rapid "high". In certain preferred embodiments, when the dosage form is tampered with and exposed to a small amount (e.g., less than about 10 ml) of an aqueous liquid (e.g., water), the dosage form will be unsuitable for injection and/or inhalation. Upon the addition of the aqueous liquid, the tampered dosage form preferably becomes thick and viscous, rendering it unsuitable for injection. The term "unsuitable for injection" is defined for purposes of the present invention to mean that one would have substantial difficulty injecting the dosage form (e.g., due to pain upon administration or difficulty pushing the dosage form through a syringe) due to the viscosity imparted on the dosage form, thereby reducing the potential for abuse of the opioid analgesic in the dosage form. In certain embodiments, the gelling agent is present in such an amount in the dosage form that attempts at evaporation (by the application of heat) to an aqueous mixture of the dosage form in an effort to produce a higher concentration of the therapeutic agent, produces a highly viscous substance unsuitable for injection.

When nasally inhaling the tampered dosage form, the gelling agent can become gel like upon administration to the nasal passages due to the moisture of the mucous membranes. This also makes such formulations aversive to nasal administration, as the gel will stick to the nasal passage and minimize absorption of the abusable substance. In certain embodiments of the present invention, the dosage form comprises a combination of any or all of the aforementioned aversive agents (e.g., a bittering agent, an irritant, and/or a gelling agent) to discourage an abuser from tampering with the dosage form and thereafter inhaling, injecting, and/or swallowing the tampered dosage form.

Embodiments specifically contemplated include bittering agent; gelling agent; irritant; bittering agent and gelling agent; bittering agent and irritant; gelling agent and irritant; and bittering agent and gelling agent and irritant.

In certain preferred embodiments, the dosage forms are controlled release oral dosage forms comprising a therapeutically effective amount of an opioid analgesic with one or more of the aversive agents described above such that the dosage form provides effective pain relief for at least about 12 hours, or at least about 24 hours when orally administered to a human patient.

In certain embodiments of the present invention the aversive agent present in the dosage form is present in a substantially non-releasable form (i.e., "sequestered") when the dosage form is administered intact as directed. Preferably, because the aversive agent is present in the dosage form in a substantially non-releasable form, it is not substantially released in the gastrointestinal tract when the dosage form is orally administered intact.

In other embodiments, the aversive agent may not be "sequestered" as disclosed above wherein the aversive agent is not released or minimally released from an intact dosage form, but may have a modified or sustained release so as not to dump the aversive agent in a particular section of the gastrointestinal tract, e.g. the stomach, where it may cause an unwanted effect such as excessive irritation. The aversive agent can be combined with an enteric carrier to delay its release or combined with a carrier to provide a sustained release of the aversive agent. However, it is contemplated in the present invention that the aversive agent will preferably not have any significant side effect (e.g., gastrointestinal side effect) even if all of the aversive agent is immediately released upon oral administration of an intact dosage form as directed.

The aversive agent(s) can also be in the dosage form in releasable form and non-releasable form in any combination. For example, a dosage form can have a bittering agent, irritant, gel or combination thereof in releasable form and non-releasable form as disclosed in U.S. Application entitled "Pharmaceutical Formulations Containing Opioid Agonist, Releasable Antagonist, and Sequestered Antagonist" filed Aug. 6, 2002, the disclosure of which is hereby incorporated by reference in its entirety.

The term "aversive agent" is defined for purposes of the present invention to mean a bittering agent, an irritant, a gelling agent, or combinations thereof.

The term "tampered dosage form" is defined for purposes of the present invention to mean that the dosage form has been manipulated by mechanical, thermal, and/or chemical means which changes the physical properties of the dosage form, e.g., to liberate the opioid agonist for immediate release if it is in sustained release form, or to make the opioid agonist available for inappropriate use such as administration by an alternate route, e.g., parenterally. The tampering can be, e.g., by means of crushing, shearing, grinding, chewing, dissolution in a solvent, heating, (e.g., greater than about 45° C.), or any combination thereof.

The term "substantially non-releasable form" for purposes of the present invention refers to an aversive agent that is not released or substantially not released at one hour after the intact dosage form containing an opioid agonist and at least one aversive agent is orally administered (i.e., without having been tampered with). The aversive agent in a substantially non-releasable form may be prepared in accordance with the teachings of U.S. application Ser. No. 09/781,081, entitled "Tamper Resistant Oral Opioid Agonist Formulations" filed Feb. 8, 2001, the disclosure of which is hereby incorporated by reference in its entirety, which describes a dosage form comprising an opioid antagonist in a substantially non-releasable form. For purposes of the present invention, the amount released after oral administration of the intact dosage form may be measured in-vitro via the dissolution at 1 hour of the dosage form in 900 ml of Simulated Gastric Fluid using a USP Type II (paddle) apparatus at 75 rpm at 37.degree. C. Such a dosage form is also referred to as comprising a "sequestered aversive agent" depending on the agent or agents which are not released or substantially not released. In certain preferred embodiments of the invention, the substantially non-releasable form of the aversive agent is resistant to laxatives (e.g., mineral oil) used to manage delayed colonic transit and resistant to achlorhydric states. Preferably, the aversive agent is not released or not substantially released 4, 8, 12 and/or 24 hours after oral administration.

The phrase "analgesic effectiveness" is defined for purposes of the present invention as a satisfactory reduction in or elimination of pain, along with a tolerable level of side effects, as determined by the human patient.

The term "sustained release" is defined for purposes of the present invention as the release of the opioid analgesic from the oral dosage form at such a rate that blood (e.g., plasma) concentrations (levels) are maintained within the therapeutic range but below toxic levels over an extended period of time, e.g., from about 12 to about 24 hours as compared to an immediate release product. Preferably the sustained release is sufficient to provide a twice-a-day or a once-a-day formulation.

The term "particles" of aversive agent, as used herein, refers to granules, spheroids, beads or pellets comprising the aversive agent. In certain preferred embodiments, the aversive agent particles are about 0.2 to about 2 mm in diameter, more preferably about 0.5 to about 2 mm in diameter.

The term "parenterally" as used herein includes subcutaneous injections, intravenous injections, intramuscular injections, intrasternal injections, infusion techniques, or other methods of injection known in the art.

The term "inhaled" as used herein includes trans-mucosal, trans-bronchial, and trans-nasal abuse.

The term "bittering agent" as used herein includes a compound used to impart a bitter taste, bitter flavor, etc., to an abuser administering a tampered dosage form of the present invention.

The term "irritant" as used herein includes a compound used to impart an irritating or burning sensation to an abuser administering a tampered dosage form of the present invention.

The term "gelling agent" as used herein includes a compound or composition used to impart gel-like or thickening quality to a tampered dosage form upon the addition of moisture or liquid.

DETAILED DESCRIPTION OF THE INVENTION

The aversive agents of the present invention are preferably for use in connection with oral dosage forms including opioid analgesics, which provide valuable analgesia but which may be abused. This is particularly true for controlled release opioid analgesic products which have a large dose of opioid analgesic intended to be released over a period of time in each dosage unit. Drug abusers typically may take a controlled-release product and crush, shear, grind, chew, dissolve and/or heat, extract or otherwise damage the product so that the full contents of the dosage form become available for immediate absorption by injection, inhalation, and/or oral consumption.

In certain embodiments, the present invention comprises a method for preventing or deterring the abuse of opioid analgesics by the inclusion of at least one aversive agent in the dosage form with the opioid analgesic.

In certain alternative embodiments, the present invention comprises a method for preventing or deterring the abuse of drugs other than opioid analgesics which may also be the subject of abuse, by including at least one of the aversive agents described herein in a dosage form comprising the drug other than an opioid analgesic which is the subject of abuse.

In certain embodiments of the present invention wherein the dosage form includes an aversive agent comprising a bittering agent, various bittering agents can be employed including, for example and without limitation, natural, artificial and synthetic flavor oils and flavoring aromatics and/or oils, oleoresins and extracts derived from plants, leaves, flowers, fruits, and so forth, and combinations thereof. Nonlimiting representative flavor oils include spearmint oil, peppermint oil, eucalyptus oil, oil of nutmeg, allspice, mace, oil of bitter almonds, menthol and the like. Useful bittering agents can be artificial, natural and synthetic fruit flavors such as citrus oils including lemon, orange, lime, grapefruit, and fruit essences and so forth. Additional bittering agents include sucrose derivatives (e.g., sucrose octaacetate), chlorosucrose derivatives, quinine sulphate, and the like. The preferred bittering agent for use in the present invention is Denatonium Benzoate NF-Anhydrous, sold under the name Bitrex™ (Macfarlan Smith Limited, Edinburgh, UK).

With the inclusion of a bittering agent in the formulation, the intake of the tampered dosage form produces a bitter taste upon inhalation or oral administration which in certain embodiments spoils or hinders the pleasure of obtaining a high from the tampered dosage form, and preferably prevents the abuse of the dosage form.

A bittering agent may be added to the formulation in an amount of less than about 50% by weight preferably less than about 10% by weight, most preferably less than about 5% by weight of the dosage form, and most preferably in an amount ranging from about 0.1 to 1.0 percent by weight of the dosage form, depending on the particular bittering agent(s) used. A dosage form including a bittering agent preferably discourages improper usage of the tampered dosage form by imparting a disagreeable taste or flavor to the tampered dosage form.

In certain embodiments of the present invention wherein the dosage form includes an aversive agent comprising an irritant, various irritants can be employed including, for example and without limitation capsaicin, a capsaicin analog with similar type properties as capsaicin, and the like. Some capsaicin analogues or derivatives include for example and without limitation, resiniferatoxin, tinyatoxin, heptanoyl-isobutylamide, heptanoyl guaiacylamide, other isobutylamides or guaiacylamides, dihydrocapsaicin, homovanillyl octylester, nonanoyl vanillylamide, or other compounds of the class known as vanilloids. Resiniferatoxin is described, for example, in U.S. Pat. No. 5,290,816 (Blumberg), issued Mar. 1, 1994. U.S. Pat. No. 4,812,446 (Brand), issued Mar. 14, 1989, describes capsaicin analogs and methods for their preparation. Further, U.S. Pat. No. 4,424,205 (LaHann et al.), issued Jan. 3, 1984, cite Newman, "Natural and Synthetic Pepper-Flavored Substances" published in 1954 as listing pungency of capsaicin-like analogs. Ton et al., British Journal of Pharmacology, 10, pp. 175-182 (1955) discuss pharmacological actions of capsaicin and its analogs.

With the inclusion of an irritant (e.g., capsaicin) in the dosage form, when the dosage form is tampered with, the capsaicin imparts a burning or discomforting quality to the abuser to preferably discourage the inhalation, injection, or oral administration of the tampered dosage form, and preferably to prevent the abuse of the dosage form. Suitable capsaicin compositions include capsaicin (trans 8-methyl-N-vanillyl-6-noneamide or analogues thereof in a concentration between about 0.00125% and 50% by weight, preferably between about 1 and about 7.5% by weight, and most preferably, between about 1 and about 5% by weight of the dosage form.

In certain embodiments of the present invention wherein the dosage form includes an aversive agent comprising a gelling agent, various gelling agents can be employed including, for example and without limitation, sugars or sugar derived alcohols, such as mannitol, sorbitol, and the like, starch and starch derivatives, cellulose derivatives, such as microcrystalline cellulose, sodium cahoxymethyl cellulose, methylcellulose, ethyl cellulose, hydroxyethyl cellulose, hydroxypropyl cellulose, and hydroxypropyl methylcellulose, attapulgites, bentonites, dextrins, alginates, carrageenan, gum tragacanth, gum acacia, guar gum, xanthan gum, pectin, gelatin, kaolin, lecithin, magnesium aluminum silicate, the carbomers and carbopols, polyvinylpyrrolidone, polyethylene glycol, polyethylene oxide, polyvinyl alcohol, silicon dioxide, surfactants, mixed surfactant/wetting agent systems, emulsifiers, other polymeric materials, and mixtures thereof, etc. In certain preferred embodiments, the gelling agent is xanthan gum. In other preferred embodiments, the gelling agent of the present invention is pectin. The pectin or pectic substances useful for this invention include not only purified or isolated pectates but also crude natural pectin sources, such as apple, citrus or sugar beet residues which have been subjected, when necessary, to esterification or de-esterification, e.g., by alkali or enzymes. Preferably, the pectins used in this invention are derived from citrus fruits such as lime, lemon, grapefruit, and orange.

With the inclusion of a gelling agent in the dosage form, when the dosage form is tampered with, the gelling agent preferably imparts a gel-like quality to the tampered dosage form which preferably spoils or hinders the pleasure of obtaining a rapid high from the tampered dosage form due to the gel like consistency in contact with the mucous membrane, and in certain embodiments, prevents the abuse of the dosage form by minimizing absorption, e.g. in the nasal passages. A gelling agent may be added to the formulation in a ratio of gelling agent to opioid agonist of from about 1:40 to about 40:1 by weight, preferably from about 1:1 to about 30:1 by weight, and more preferably from about 2:1 to about 10:1 by weight of the opioid agonist. In certain alternative embodiments, the gelling agent may be present in a ratio to the opioid agonist of from about 1:15 to about 15:1, preferably in a ratio of from about 1:8 to about 8:1, and more preferably from about 1:3 to about 3:1 by weight of the opioid agonist.

In certain other embodiments, the dosage form forms a viscous gel after the dosage form is tampered with, dissolved in an aqueous liquid (from about 0.5 to about 10 ml and preferably from 1 to about 5 ml), causing the resulting mixture to have a viscosity of at least about 10 cP. Most preferably, the resulting mixture will have a viscosity of at least about 60 cP.

In certain other embodiments, the dosage form forms a viscous gel after the dosage form is tampered with, dissolved in an aqueous liquid (from about 0.5 to about 10 ml and preferably from 1 to about 5 ml) and then heated (e.g., greater than about 45° C.), causing the resulting mixture to have a viscosity of at least about 10 cP. Most preferably, the resulting mixture will have a viscosity of at least about 60 cP.

In certain embodiments, the dosage form may include one or more of the aforementioned aversive agents. For safety reasons, the amount of the bittering agent, irritant, or gelling agent in a formulation of the present invention should not be toxic to humans.

In certain embodiments, the aversive agent included in the dosage form may be in a substantially non-releasable form. Where the aversive agent is in a substantially non-releasable form, the substantially non-releasable form of the aversive agent comprises an aversive agent that is formulated with one or more pharmaceutically acceptable hydrophobic materials, such that the aversive agent is not released or substantially not released during its transit through the gastrointestinal tract when administered orally as intended, without having been tampered with.

In certain embodiments of the present invention, the substantially non-releasable form of the aversive agent is vulnerable to mechanical, thermal and/or chemical tampering, e.g., tampering by means of crushing, shearing, grinding, chewing and/or dissolution in a solvent in combination with heating (e.g., greater, than about 45° C.) of the oral dosage form. When the dosage form is tampered with, the integrity of the substantially non-releasable form of the aversive agent will be compromised, and the aversive agent will be made available to be released. In certain embodiments, when the dosage form is chewed, crushed or dissolved and heated in a solvent, the release of the aversive agent hinders, deters or prevents the administration of the tampered dosage form orally, intranasally, parenterally and/or sublingually.

The opioid agonists useful in the present invention include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, mixtures of any of the foregoing, salts of any of the foregoing, and the like. In certain embodiments, the amount of the opioid agonist in the claimed opioid composition may be about 75 ng to about 750 mg.

In certain preferred embodiments, the opioid agonist is selected from the group consisting of hydrocodone, morphine, hydromorphone, oxycodone, codeine, levorphanol, meperidine, methadone, oxymorphone, buprenorphine, fentanyl and derivatives thereof, dipipanone, heroin, tramadol, etorphine, dihydroetorphine, butorphanol, levorphanol, or salts thereof or mixtures thereof. In certain preferred embodiments, the opioid agonist is oxycodone or hydrocodone.

In embodiments in which the opioid analgesic comprises hydrocodone, dosage forms may include analgesic doses from about 2 mg to about 50 mg of hydrocodone bitartrate. In embodiments in which the opioid analgesic comprises hydromorphone the dosage form may include from about 2 mg to about 64 mg hydromorphone hydrochloride. In embodiments in which the opioid analgesic comprises morphine, the dosage form may include from about 2.5 mg to about 800 mg morphine sulfate, by weight. In embodiments in which the opioid analgesic comprises oxycodone, the dosage form may include from about 2.5 mg to about 320 mg oxycodone hydrochloride. The dosage form may contain more than one opioid analgesic to provide a therapeutic effect. Alternatively, the dosage form may contain molar equivalent amounts of other salts of the opioids useful in the present invention.

Hydrocodone is a semisynthetic narcotic analgesic and antitussive with multiple central nervous system and gastrointestinal actions. Chemically, hydrocodone is 4,5-epoxy-3-methoxy-17-methylmorphinan-6-one, and is also known as dihydrocodeinone. Like other opioids, hydrocodone may be habit forming and may produce drug dependence of the morphine type. In excess doses hydrocodone, like other opium derivatives, will depress respiration.

Oral hydrocodone is also available in Europe (Belgium, Germany, Greece, Italy, Luxembourg, Norway and Switzerland) as an antitussive agent. A parenteral formulation is also available in Germany as an antitussive agent. For use as an analgesic, hydrocodone bitartrate is commercially available in the United States only as a fixed combination with non-opiate drugs (i.e., ibuprofen, acetaminophen, aspirin, etc.) for relief of moderate or moderately severe pain.

A common dosage form of hydrocodone is in combination with acetaminophen, and is commercially available, e.g., as Lortab® in the U.S. from UCB Pharma. Inc. as 2.5/500 mg, 5/500 mg, 7.5/500 mg and 10/500 mg hydrocodone/acetaminophen tablets. Tablets are also available in the ratio of 7.5 mg hydrocodone bitartrate and 650 mg acetaminophen; and 7.5 mg hydrocodone bitartrate and 750 mg acetaminophen. Hydrocodone in combination with aspirin is given in an oral dosage form to adults generally in 1-2 tablets every 4-6 hours as needed to alleviate pain. The tablet form is 5 mg hydrocodone bitartrate and 224 mg aspirin with 32 mg caffeine; or 5 mg hydrocodone bitartrate and 500 mg aspirin. A relatively new formulation comprises hydrocodone bitartrate and ibuprofen. Vicoprofen®, commercially available in the U.S. from Knoll Laboratories, is a tablet containing 7.5 mg hydrocodone bitartrate and 200 mg ibuprofen. The present invention is contemplated to encompass all such formulations, with the inclusion of one or more aversive agents as described herein.

Oxycodone, chemically known as 4,5-expoxy-14-hydroxy-3-methoxy-17-methylmorphinan-6-one, is an opioid agonist whose principal therapeutic action is analgesia. Other therapeutic effects of oxycodone include anxiolysis, euphoria and feelings of relaxation. The precise mechanism of its analgesic action is not known, but specific CNS opioid receptors for endogenous compounds with opioid-like activity have been identified throughout the brain and spinal cord and play a role in the analgesic effects of this drug.

Oxycodone is commercially available in the United States, e.g., as Oxycontin.® from Purdue Pharma L.P. as controlled-release tablets for oral administration containing 10 mg, 20 mg, 40 mg or 80 mg oxycodone hydrochloride, and as OxyIR®, also from Purdue Pharma L.P., as immediate-release capsules containing 5 mg oxycodone hydrochloride. The present invention is contemplated to encompass all such formulations, with the inclusion of one or more aversive agents as described herein.

Additionally, agents other than opioid analgesics which are subject to abuse may be used in accordance with the present invention in place of the opioid analgesics in the dosage form. Certain agents include, for example and without limitation, tranquilizers, CNS depressants, CNS stimulants, sedative hypnotics and the like. More specifically, barbiturates such as phenobarbital, secobarbital, pentobarbital, butabarbital, talbutal, aprobarbital, mephobarbital, butalbital, pharmaceutically acceptable salts thereof, and the like; benzodiazepines such as diazepam, chlordiazepoxide, alprazolam, triazolam, estazolam, clonazepam, flunitrazepam, pharmaceutically acceptable salts thereof, and the like; stimulants such as gamma-hydroxybutyrate, dextroamphetamine, methylphenidate, sibutramine, methylenedioxymethamphetamine, pharmaceutically acceptable salts thereof, and the like; and other agents such as marinol, meprobamate, carisoprodol, pharmaceutically acceptable salts thereof and the like.

Preparation of Aversive Agent in a Substantially Non-Releasable Form

In certain embodiments of the present invention, an aversive agent in a substantially non-releasable form may be prepared by combining the aversive agent with one or more of a pharmaceutically acceptable hydrophobic material. For example, aversive agent particles may be coated with coating that substantially prevents the release of the aversive agent, the coating comprising the hydrophobic materials(s). Another example would be an aversive agent that is dispersed in a matrix that renders the aversive agent substantially non-releasable, the matrix comprising the hydrophobic materials(s). In certain embodiments, the pharmaceutically acceptable hydrophobic material comprises a cellulose polymer selected from the group consisting of ethylcellulose, cellulose acetate, cellulose propionate (lower, medium or higher molecular weight), cellulose acetate propionate, cellulose acetate butyrate, cellulose acetate phthalate and cellulose triacetate. An example of ethylcellulose is one that has an ethoxy content of 44 to 55%. Ethylcellulose may be used in the form of an alcoholic solution. In certain other embodiments, the hydrophobic material comprises polylactic acid, polyglycolic acid or a copolymer of the polylactic and polyglycolic acid.

In certain embodiments, the hydrophobic material may comprise a cellulose polymer selected from the group consisting of cellulose ether, cellulose ester, cellulose ester ether, and cellulose. The cellulosic polymers have a degree of substitution, D.S., on the anhydroglucose unit, from greater than zero and up to 3 inclusive. By degree of substitution is meant the average number of hydroxyl groups present on the anhydroglucose unit comprising the cellulose polymer that are replaced by a substituting group. Representative materials include a polymer selected from the group consisting of cellulose acylate, cellulose diacylate, cellulose triacylate, cellulose acetate, cellulose diacetate, cellulose triacetate, mono, di, and tricellulose alkanylates, mono, di, and tricellulose aroylates, and mono, di, and tricellulose alkenylates. Exemplary polymers include cellulose acetate having a D.S. and an acetyl content up to 21%; cellulose acetate having an acetyl content up to 32 to 39.8%; cellulose acetate having a D.S. of 1 to 2 and an acetyl content of 21 to 35%; cellulose acetate having a D.S. of 2 to 3 and an acetyl content of 35 to 44.8%.

More specific cellulosic polymers include cellulose propionate having a D.S. of 1.8 and a propyl content of 39.2 to 45 and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylate having a D.S. of 2.9 to 3 such as cellulose triacetate, cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentanoate, and coesters of cellulose such as cellulose acetate butyrate, cellulose acetate octanoate butyrate and cellulose acetate propionate.

Additional cellulose polymers useful for preparing an aversive agent in a substantially non-releasable form include acetaldehyde dimethyl cellulose acetate, cellulose acetate ethylcarbamate, cellulose acetate methylcarbamate, and cellulose acetate dimethylaminocellulose acetate.

Acrylic polymers useful for preparation of the aversive agent in a substantially non-releasable form include, but are not limited to, acrylic resins comprising copolymers synthesized from acrylic and methacrylic acid esters (e.g., the copolymer of acrylic acid lower alkyl ester and methacrylic acid lower alkyl ester) containing about 0.02 to 0.03 mole of a tri (lower alkyl) ammonium group per mole of the acrylic and methacrylic monomers used. An example of a suitable acrylic resin is a polymer manufactured by Rohm Pharma GmbH and sold under the Eudragit® RS trademark. Eudragit RS30D is preferred. Eudragit® RS is a water insoluble copolymer of ethyl acrylate (EA), methyl methacrylate (MM) and trimethylammoniumethyl methacrylate chloride (TAM) in which the molar ratio of TAM to the remaining components (EA and MM) is 1:40. Acrylic resins such as Eudragit® RS may be used in the form of an aqueous suspension.

In certain embodiments of the invention, the acrylic polymer may be selected from the group consisting of acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate)

copolymer, polyacrylamide, aminoalkyl methacrylate copolymer, poly(methacrylic acid anhydride), and glycidyl methacrylate copolymers.

When the aversive agent in a substantially non-releasable form comprises aversive agent particles coated with a coating that renders the aversive agent substantially non-releasable, and when a cellulose polymer or an acrylic polymer is used for preparation of the coating composition, suitable plasticizers, e.g., acetyl triethyl citrate and/or acetyl tributyl citrate may also be admixed with the polymer. The coating may also contain additives such as coloring agents, talc and/or magnesium stearate, which are well known in the coating art.

The coating composition may be applied onto the aversive agent particles by spraying it onto the particles using any suitable spray equipment known in the art. For example, a Wuster fluidized-bed system may be used in which an air jet, injected from underneath, fluidizes the coated material and effects drying while the insoluble polymer coating is sprayed on. The thickness of the coating will depend on the characteristics of the particular coating composition being used. However, it is well within the ability of one skilled in the art to determine by routine experimentation the optimum thickness of a particular coating required for a particular dosage form of the present invention.

The pharmaceutically acceptable hydrophobic material useful for preparing an aversive agent in a substantially non-releasable form includes a biodegradable polymer comprising a poly(lactic/glycolic acid) ("PLGA"), a polylactide, a polyglycolide, a polyanhydride, a polyorthoester, polycaprolactones, polyphosphazenes, polysaccharides, proteinaceous polymers, polyesthers, polydioxanone, polygluconate, polylactic-acid-polyethylene oxide copolymers, poly(hydroxybutyrate), polyphosphoesther or mixtures or blends of any of these.

In certain embodiments, biodegradable polymer comprises a poly (lactic/glycolic acid), a copolymer of lactic and glycolic acid, having molecular weight of about 2,000 to about 500,000 daltons. The ratio of lactic acid to glycolic acid is from about 100:0 to about 25:75, with the ratio of lactic acid to glycolic acid of 65:35 being preferred.

Poly(lactic/glycolic acid) may be prepared by the procedure set forth in U.S. Pat. No. 4,293,539 (Ludwig et al.), the disclosure of which is hereby incorporated by reference in its entirety. In brief, Ludwig prepares the copolymer by condensation of lactic acid and glycolic acid in the presence of a readily removable polymerization catalyst (e.g., a strong acid ion-exchange resin such as Dowex HCR-W2-H). The amount of catalyst is not critical to the polymerization, but typically is from about 0.01 to about 20 parts by weight relative to the total weight of combined lactic acid and glycolic acid. The polymerization reaction may be conducted without solvents at a temperature from about 100° C. to about 250° C. for about 48 to about 96 hours, preferably under a reduced pressure to facilitate removal of water and by-products. Poly (lactic/glycolic acid) is then recovered by filtering the molten reaction mixture in an organic solvent such as dichloromethane or acetone and then filtering to remove the catalyst.

Once the aversive agent in a substantially non-releasable form is prepared, it may be combined with an opioid agonist, along with conventional excipients known in the art, to prepare the oral dosage form of the present invention. It is contemplated that a bittering agent or capsaicin would be the most likely aversive agent to be included in a sequestered formulation. The polymers and other ingredients above may also be utilized to formulate the aversive agents to slow release or delay release as disclosed above.

In certain preferred embodiments of the invention, the oral dosage form is a capsule or a tablet. When being formulated as a tablet, the aversive agent and opioid agonist may be combined with one or more inert, non-toxic pharmaceutical excipients which are suitable for the manufacture of tablets. Such excipients include, for example, an inert diluent such as lactose; granulating and disintegrating agents such as cornstarch; binding agents such as starch; and lubricating agents such as magnesium stearate.

The oral dosage form of the present invention may be formulated to provide immediate release of the opioid agonist contained therein. In other embodiments of the invention, however, the oral dosage form provides sustained-release of the opioid agonist.

In certain embodiments, the oral dosage forms providing sustained release of the opioid agonist may be prepared by admixing the aversive agent in a substantially non-releasable form with the opioid agonist and desirable pharmaceutical excipients to provide a tablet, and then coating the tablet with a sustained-release tablet coating.

In certain embodiments of the invention, sustained release opioid agonist tablets may be prepared by admixing the substantially non-releasable form of an aversive agent with an aversive agent in a matrix that provides the tablets with sustained-releasing properties.

Dosage Forms

The opioid analgesic formulation in combination with one or more aversive agents can be formulated as an immediate release formulation or controlled release oral formulation in any suitable tablet, coated tablet or multiparticulate formulation known to those skilled in the art. The controlled release dosage form may include a controlled release material which is incorporated into a matrix along with the opioid analgesic. In addition, the aversive agent may be separate from the matrix, or incorporated into the matrix.

The controlled release dosage form may optionally comprise particles containing or comprising the opioid analgesic, wherein the particles have diameter from about 0.1 mm to about 2.5 mm, preferably from about 0.5 mm to about 2 mm. Additionally, the aversive agent may be incorporated into these particles, or may be incorporated into a tablet or capsule containing these particles. Preferably, the particles are film coated with a material that permits release of the opioid analgesic at a controlled rate in an environment of use. The film coat is chosen so as to achieve, in combination with the other stated properties, a desired in-vitro release rate. The controlled release coating formulations of the present invention should be capable of producing a strong, continuous film that is smooth and elegant, capable of supporting pigments and other coating additives, non-toxic, inert, and tack-free.

In certain embodiments, the dosage forms of the present invention comprise normal release matrixes containing the opioid analgesic and the aversive agent.

Coated Beads

In certain embodiments of the present invention a hydrophobic material is used to coat inert pharmaceutical beads such as nu panel 18/20 beads comprising an opioid analgesic, and a plurality of the resultant solid controlled release beads may thereafter be placed in a gelatin capsule in an amount sufficient to provide an effective controlled release dose when ingested and contacted by an environmental fluid, e.g., gastric fluid or dissolution media. The one or more aversive agents may also be coated onto the beads comprising the opioid analgesic, may be prepared as separate beads and then combined in a dosage form including the controlled release beads comprising an opioid analgesic, or the one or more aversive agents may be mixed in the dosage form with the controlled release beads comprising the opioid analgesic. In preferred embodiments where the opioid analgesic and the aversive agent are mixed in a capsule as different beads, the beads have an exact or similar appearance in order to deter an abuser from manually separating the beads prior to abuse in order to avoid the aversive substance. In tablet dosage forms, the aversive agent is preferably not included as a distinct layer which can be easier to separate from the active agent, although the present invention docs encompass these embodiments.

The controlled release bead formulations of the present invention slowly release the opioid analgesic, e.g., when ingested and exposed to gastric fluids, and then to intestinal fluids. The controlled release profile of the formulations of the invention can be altered, for example, by varying the amount of overcoating with the hydrophobic material, altering the manner in which a plasticizer is added to the hydrophobic material, by varying the amount of plasticizer relative to hydrophobic material, by the inclusion of additional ingredients or excipients, by altering the method of manufacture, etc. The dissolution profile of the ultimate product may also be modified, for example, by increasing or decreasing the thickness of the retardant coating.

Spheroids or beads coated with an opioid analgesic are prepared, e.g., by dissolving the opioid analgesic in water and then spraying the solution onto a substrate, for example, nu pariel 18/20 beads, using a Wuster insert. Thereafter, the one or more aversive agent is optionally added to the beads prior to coating. Optionally, additional ingredients are also added prior to coating the beads in order to assist the binding of the opioid to the beads. For example, a product which includes hydroxypropylmethylcellulose, etc. (e.g., Opadry®, commercially available from Colorcon, Inc.) may be added to the solution and the solution mixed (e.g., for about 1 hour) prior to application of the same onto the beads. The resultant coated substrate, in this example beads, may then be optionally overcoated with a barrier agent, to separate the opioid analgesic from the hydrophobic controlled release coating. An example of a suitable barrier agent is one which comprises hydroxypropylmethylcellulose. However, any film-former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticizer, e.g. triethyl citrate. Pre-formulated aqueous dispersions of ethylcellulose, such as Aquacoat® or Surelease®, may be used. If Surelease® is used, it is not necessary to separately add a plasticizer. Alternatively, pre-formulated aqueous dispersions of acrylic polymers such as Eudragit® can be used.

Plasticized hydrophobic material may be applied onto the substrate comprising the opioid analgesic by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the hydrophobic material to obtain a predetermined controlled release of said opioid analgesic when the coated substrate is exposed to aqueous solutions, e.g. gastric fluid, is preferably applied, taking into account the physical characteristics of the opioid analgesic, the manner of incorporation of the plasticizer, etc. After coating with the hydrophobic material, a further overcoat of a film-former, such as Opadry®, is optionally applied to the beads. This overcoat is provided, if at all, in order to substantially reduce agglomeration of the beads.

The release of the opioid analgesic from the controlled release formulation of the present invention can be further influenced, i.e., adjusted to a desired rate, by the addition of one or more release-modifying agents, or by providing one or more passageways through the coating. The ratio of hydrophobic material to water soluble material is determined by, among other factors, the release rate required and the solubility characteristics of the materials selected.

The release-modifying agents which function as pore-formers may be organic or inorganic, and include materials that can be dissolved, extracted or leached from the coating in the environment of use. The pore-formers may comprise one or more hydrophilic materials such as hydroxypropylmethylcellulose.

The controlled release coatings of the present invention can also include erosion-promoting agents such as starch and gums.

The controlled release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semipermeable polymer.

In certain preferred embodiments, the release-modifying agent is selected from hydroxypropylmethylcellulose, lactose, metal stearates, and mixtures of any of the foregoing.

The controlled release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864. The passageway can have any shape such as round, triangular, square, elliptical, irregular, etc.

Matrix Formulations

In certain embodiments of the present invention, the sustained release formulation is achieved via a matrix optionally having a controlled release coating as set forth herein. The present invention may also utilize a sustained release matrix that affords in-vitro dissolution rates of the opioid analgesic within desired ranges and releases the opioid analgesic in a pH-dependent or pH-independent manner.

A non-limiting list of suitable sustained-release materials which may be included in a sustained-release matrix according to the invention includes hydrophilic and/or hydrophobic materials, such as gums, cellulose ethers, acrylic resins, protein derived materials, waxes, shellac, and oils such as hydrogenated castor oil and hydrogenated vegetable oil. However, any pharmaceutically acceptable hydrophobic or hydrophilic sustained-release material which is capable of imparting sustained-release of the opioid analgesic may be used in accordance with the present invention. Preferred sustained-release polymers include alkylcelluloses such as ethylcellulose, acrylic and methacrylic acid polymers and copolymers; and cellulose ethers, especially hydroxyalkylcelluloses (especially hydroxypropylmethylcellulose) and carboxyalkylcelluloses. Preferred acrylic and methacrylic acid polymers and copolymers include methyl methacrylate, methyl methacrylate copolymers, ethoxyethyl methacrylates, ethyl acrylate, trimethyl ammonioethyl methacrylate, cyanoethyl methacrylate, aminoalkyl methacrylate copolymer, poly(acrylic acid), poly(methacrylic acid), methacrylic acid alkylamine copolymer, poly(methylmethacrylate), poly(methacrylicacid) (anhydride), polymethacrylate, polyacrylamide, poly(methacrylic acid anhydride), and glycidyl methacrylate copolymers. Certain preferred embodiments utilize mixtures of any of the foregoing sustained-release materials in the matrix of the invention.

The matrix also may include a binder. In such embodiments, the binder preferably contributes to the sustained-release of the opioid analgesic or pharmaceutically acceptable salt thereof from the sustained-release matrix.

If an additional hydrophobic binder material is included, it is preferably selected from natural and synthetic waxes, fatty acids, fatty alcohols, and mixtures of the same. Examples include beeswax, carnauba wax, stearic acid and stearyl alcohol. This list is not meant to be exclusive. In certain preferred embodiments, a combination of two or more hydrophobic binder materials are included in the matrix formulations.

Preferred hydrophobic binder materials which may be used in accordance with the present invention include digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils, natural and synthetic waxes and polyalkylene glycols. Hydrocarbons having a melting point of between 25° and 90° C. are preferred. Of the long-chain hydrocarbon binder materials, fatty (aliphatic) alcohols are preferred in certain embodiments. The oral dosage form may contain up to 80% (by weight) of at least one digestible, long chain hydrocarbon.

In certain embodiments, the hydrophobic binder material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic acid, stearyl alcohol and hydrophobic and hydrophilic materials having hydrocarbon backbones. Suitable waxes include, for example, beeswax, glycowax, castor wax and carnauba wax. For purposes of the present invention, a wax-like substance is defined as any material which is normally solid at room temperature and has a melting point of from about 30 to about 100° C. In certain preferred embodiments, the dosage form comprises a sustained release matrix comprising an opioid analgesic; one or more aversive agents; and at least one water soluble hydroxyalkyl cellulose, at least one $C_{12}$-$C_{36}$, preferably $C_{14}$-$C_{22}$, aliphatic alcohol and, optionally, at least one polyalkylene glycol. The hydroxyalkyl cellulose is preferably a hydroxy ($C_1$ to $C_6$) alkyl cellulose, such as hydroxypropylcellulose, hydroxypropylmethylcellulose and, especially, hydroxyethyl cellulose. The amount of the at least one hydroxyalkyl cellulose in the present oral dosage form may be determined, inter alia, by the precise rate of opioid analgesic release required. The aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the aliphatic alcohol in the present oral dosage form may be determined, as above, by the precise rate of opioid analgesic release required. It may also depend on whether at least one polyalkylene glycol is present in or absent from the oral dosage form. In the absence of at least one polyalkylene glycol, the oral dosage form preferably contains between about 20% and about 50% (by wt) of the aliphatic alcohol. When a polyalkylene glycol is present in the oral dosage form, then the combined weight of the aliphatic alcohol and the polyalkylene glycol preferably constitutes between about 20% and about 50% (by wt) of the total dosage form.

In one preferred embodiment, the ratio of, e.g., the at least one hydroxyalkyl cellulose or acrylic resin to the at least one aliphatic alcohol/polyalkylene glycol determines, to a considerable extent, the release rate of the opioid analgesic from the formulation. In certain embodiments, a ratio of the hydroxyalkyl cellulose to the aliphatic alcohol/polyalkylene glycol of between 1:1 and 1:4 is preferred, with a ratio of between 1:2 and 1:3 being particularly preferred.

In certain embodiments, the polyalkylene glycol may be, for example, polypropylene glycol, or polyethylene glycol which is preferred. The average molecular weight of the at least one polyalkylene glycol is preferably between 1,000 and 15,000, especially between 1,500 and 12,000.

Another suitable sustained-release matrix comprises an alkylcellulose (especially ethylcellulose), a $C_{12}$ to $C_{35}$ aliphatic alcohol and, optionally, a polyalkylene glycol.

In addition to the above ingredients, a sustained-release matrix may also contain suitable quantities of other materials, e.g., diluents, lubricants, binders, granulating aids, and glidants that are conventional in the pharmaceutical art.

In order to facilitate the preparation of a solid, sustained-release oral dosage form according to this invention there is provided, in a further aspect of the present invention, a process for the preparation of a solid, sustained-release oral dosage form according to the present invention comprising incorporating an opioid analgesic in a sustained-release matrix. Incorporation in the matrix may be effected, for example, by:

(a) forming granules comprising at least one hydrophobic and/or hydrophilic material as set forth above (e.g., a water soluble hydroxyalkyl cellulose) together with the opioid analgesic, and at least one aversive agent;

(b) mixing the at least one hydrophobic and/or hydrophilic material containing granules with at least one $C_{12}$-$C_{36}$ aliphatic alcohol, and (c) optionally, compressing and shaping the granules.

The granules may be formed by any of the procedures well-known to those skilled in the art of pharmaceutical formulation. For example, in one preferred method, the granules may be formed by wet granulating the hydroxyalkyl cellulose, opioid analgesic, and one or more aversive agents with water. In a particularly preferred embodiment of this process, the amount of water added during the wet granulation step is preferably between 1.5 and 5 times, especially between 1.75 and 3.5 times, the dry weight of the opioid analgesic. Optionally, the opioid analgesic and/or the one or more aversive agents are added extragranularly.

A sustained-release matrix can also be prepared by, e.g., melt-granulation or melt-extrusion techniques. Generally, melt-granulation techniques involve melting a normally solid hydrophobic binder material, e.g., a wax, and incorporating a powdered drug therein. To obtain a sustained release dosage form, it may be necessary to incorporate a hydrophobic sustained-release material, e.g. ethylcellulose or a water-insoluble acrylic polymer, into the molten wax hydrophobic binder material. Examples of sustained-release formulations prepared via melt-granulation techniques are found, e.g., in U.S. Pat. No. 4,861,598.

The additional hydrophobic binder material may comprise one or more water-insoluble wax-like thermoplastic substances possibly mixed with one or more wax-like thermoplastic substances being less hydrophobic than said one or more water-insoluble wax-like substances. In order to achieve sustained release, the individual wax-like substances in the formulation should be substantially non-degradable and insoluble in gastrointestinal fluids during the initial release phases. Useful water-insoluble wax-like binder substances may be those with a water-solubility that is lower than about 1:5,000 (w/w).

The preparation of a suitable melt-extruded matrix according to the present invention may, for example, include the steps of blending the opioid analgesic and at least one aversive agent, together with a sustained release material and preferably a binder material to obtain a homogeneous mixture. The homogeneous mixture is then heated to a temperature sufficient to at least soften the mixture sufficiently to extrude the same. The resulting homogeneous mixture is then extruded, e.g., using a twin-screw extruder, to form strands. The extrudate is preferably cooled and cut into multiparticulates by any means known in the art. The matrix multiparticulates are then divided into unit doses. The extrudate preferably has a diameter of from about 0.1 to about 5 mm and provides sustained release of the opioid analgesic or pharmaceutically acceptable salt thereof for a time period of at least about 12 hours.

An optional process for preparing the melt extruded formulations of the present invention includes directly metering into an extruder a hydrophobic sustained release material, the opioid analgesic, one or more aversive agents, and an optional binder material; heating the homogenous mixture; extruding the homogenous mixture to thereby form strands; cooling the strands containing the homogeneous mixture; cutting the strands into matrix multiparticulates having a size from about 0.1 mm to about 12 mm; and dividing said particles into unit doses. In this aspect of the invention, a relatively continuous manufacturing procedure is realized.

Optionally, the one or more aversive agents may be added to a dosage form including multiparticulates comprising opioid analgesic (without the one or more aversive agents).

Plasticizers, such as those described above, may be included in melt-extruded matrices. The plasticizer is preferably included as from about 0.1 to about 30% by weight of the matrix. Other pharmaceutical excipients, e.g., talc, mono or poly saccharides, lubricants and the like may be included in the sustained release matrices of the present invention as desired. The amounts included will depend upon the desired characteristic to be achieved.

The diameter of the extruder aperture or exit port can be adjusted to vary the thickness of the extruded strands. Furthermore, the exit part of the extruder need not be round; it can be oblong, rectangular, etc. The exiting strands can be reduced to particles using a hot wire cutter, guillotine, etc.

A melt extruded matrix multiparticulate system can be, for example, in the form of granules, spheroids or pellets depending upon the extruder exit orifice. For purposes of the present invention, the terms "melt-extruded matrix multiparticulate(s)" and "melt-extruded matrix multiparticulate system(s)" and "melt-extruded matrix particles" shall refer to a plurality of units, preferably within a range of similar size and/or shape and containing one or more active agents and one or more excipients, preferably including a hydrophobic sustained release material as described herein. Preferably the melt-extruded matrix multiparticulates will be of a range of from about 0.1 to about 12 mm in length and have a diameter of from about 0.1 to about 5 mm. In addition, it is to be understood that the melt-extruded matrix multiparticulates can be any geometrical shape within this size range. In certain embodiments, the extrudate may simply be cut into desired lengths and divided into unit doses of the therapeutically active agent without the need of a spheronization step.

In one preferred embodiment, oral dosage forms are prepared that include an effective amount of melt-extruded matrix multiparticulates within a capsule. For example, a plurality of the melt-extruded matrix multiparticulates may be placed in a gelatin capsule in an amount sufficient to provide an effective sustained release dose when ingested and contacted by gastrointestinal fluid.

In another embodiment, a suitable amount of the multiparticulate extrudate is compressed into an oral tablet using conventional tableting equipment using standard techniques. Techniques and compositions for making tablets (compressed and molded), capsules (hard and soft gelatin) and pills are also described in *Remington's Pharmaceutical Sciences*, (Arthur Osol, editor), 1553-1593 (1980).

In yet another preferred embodiment, the extrudate can be shaped into tablets as set forth in U.S. Pat. No. 4,957,681 (Klimesch, et. al.).

Optionally, the sustained-release matrix multiparticulate systems, tablets, or capsules can be coated with a sustained release coating such as the sustained release coatings described herein. Such coatings preferably include a sufficient amount of hydrophobic and/or hydrophilic sustained-release material to obtain a weight gain level from about 2 to about 25 percent, although the overcoat may be greater depending upon, e.g., the desired release rate. The coating can optionally contain one or more of the aversive agents. In such embodiments, an optional second overcoat can be applied as to minimize the perception of the aversive agent when a dosage form of the present invention is administered intact.

The dosage forms of the present invention may further include combinations of melt-extruded matrix multiparticulates containing an opioid analgesic; one or more aversive agents; or mixtures thereof. Furthermore, the dosage forms can also include an amount of an immediate release opioid analgesic for prompt therapeutic effect. The immediate release opioid analgesic may be incorporated, e.g., as separate multiparticulates within a gelatin capsule, or may be coated on the surface of, e.g., melt extruded matrix multiparticulates.

The sustained-release profile of the melt-extruded formulations of the invention can be altered, for example, by varying the amount of sustained-release material, by varying the amount of plasticizer relative to other matrix constituents, by varying the amount of hydrophobic material, by the inclusion of additional ingredients or excipients, by altering the method of manufacture, etc.

In other embodiments of the invention, melt-extruded formulations are prepared without the inclusion of the opioid analgesic; one or more aversive agents; or mixtures thereof; which is added thereafter to the extrudate. Such formulations typically will have the opioid analgesic; one or more aversive agents; or mixtures thereof blended together with the extruded matrix material, and then the mixture would be tableted in order to provide a slow release formulation. Such formulations may be advantageous, for example, when the opioid analgesic; one or more aversive agents; or mixtures thereof included in the formulation is sensitive to temperatures needed for softening the hydrophobic material and/or the retardant material.

Typical melt-extrusion production systems suitable for use in accordance with the present invention include a suitable extruder drive motor having variable speed and constant torque control, start-stop controls, and a meter. In addition, the production system will include a temperature control console which includes temperature sensors, cooling means and temperature indicators throughout the length of the extruder. In addition, the production system will include an extruder such as a twin-screw extruder which consists of two counter-rotating intermeshing screws enclosed within a cylinder or barrel having an aperture or die at the exit thereof.

The feed materials enter through a feed hopper and are moved through the barrel by the screws and are forced through the die into strands which are thereafter conveyed such as by a continuous movable belt to allow for cooling and being directed to a pelletizer or other suitable device to render the extruded ropes into the matrix multiparticulate system. The pelletizer can consist of rollers, fixed knife; rotating cutter and the like. Suitable instruments and systems are available from distributors such as C.W. Brabender Instruments, Inc. of South Hackensack, N.J. Other suitable apparatus will be apparent to those of ordinary skill in the art.

A further aspect of the invention is related to the preparation of melt-extruded matrix multiparticulates as set forth above in a manner which controls the amount of air included in the extruded product. By controlling the amount of air included in the extrudate, the release rate of the opioid analgesic, one or more aversive agents, or mixtures thereof may be altered.

Thus, in a further aspect of the invention, the melt-extruded product is prepared in a manner which substantially excludes air during the extrusion phase of the process. This may be accomplished, for example, by using a Leistritz extruder having a vacuum attachment. The extruded matrix multiparticulates prepared according to the invention using the Leistritz extruder under vacuum provides a melt-extruded product having different physical characteristics. In particular, the extrudate is substantially non-porous when magnified, e.g., using a scanning electron microscope which provides an SEM (scanning electron micrograph). Such substantially non-porous formulations may provide a faster release of the therapeutically active agent, relative to the same formulation prepared without vacuum. SEMs of the matrix multiparticulates prepared using an extruder under vacuum appear very smooth, and the multiparticulates tend to be more robust than those multiparticulates prepared without vacuum. It has been observed that in at least certain formulations, the use of extrusion under vacuum provides an extruded matrix multiparticulate product which is more pH-dependent than its counterpart formulation prepared without vacuum.

Alternatively, the melt-extruded product is prepared using a Werner-Pfleiderer twin screw extruder.

In certain embodiments, a spheronizing agent is added to a granulate or matrix multiparticulate and then spheronized to produce sustained release spheroids. The spheroids are then optionally overcoated with a sustained release coating by methods such as those described above.

Spheronizing agents which may be used to prepare the matrix multiparticulate formulations of the present invention include any art-known spheronizing agent. Cellulose derivatives are preferred, and microcrystalline cellulose is especially preferred. A suitable microcrystalline cellulose is, for example, the material sold as Avicel PH 101 (TradeMark, FMC Corporation). The spheronizing agent is preferably included as about 1 to about 99% of the matrix multiparticulate by weight.

In certain embodiments, in addition to the opioid analgesic, one or more aversive agents, and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxy propyl cellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose.

In certain embodiments, a sustained release coating is applied to the sustained release spheroids, granules, or matrix multiparticulates. In such embodiments, the sustained-release coating may include a water insoluble material such as (a) a wax, either alone or in admixture with a fatty alcohol; or (b) shellac or zein. The coating is preferably derived from an aqueous dispersion of the hydrophobic sustained release material.

In certain embodiments, it is necessary to overcoat the sustained release spheroids, granules, or matrix multiparticulates comprising the opioid analgesic, one or more aversive agents, and sustained release carrier with a sufficient amount of the aqueous dispersion of, e.g., alkylcellulose or acrylic polymer, to obtain a weight gain level from about 2 to about 50%, e.g., about 2 to about 25%, in order to obtain a sustained-release formulation. The overcoat may be lesser or greater depending upon, e.g., the desired release rate, the inclusion of plasticizer in the aqueous dispersion and the manner of incorporation of the same. Cellulosic materials and polymers, including alkylcelluloses, are sustained release materials well suited for coating the sustained release spheroids, granules, or matrix multiparticulates according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating according to the invention.

One commercially available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly to the sustained release spheroids, granules, or matrix multiparticulates.

In other preferred embodiments of the present invention, the sustained release material comprising the sustained-release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in the National Formulary (NF) XVII as fully polymerized copolymers of acrylic and methacrylic acid esters with a low content of quaternary ammonium groups. In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from Rohm GMBH and Co. Kg Darmstadt, Germany. There are several different types of Eudragit®. For example, Eudragit E is an example of a methacrylic acid copolymer which swells and dissolves in acidic media. Eudragit L is a methacrylic acid copolymer which does not swell at about pH<5.7 and is soluble at about pH>6. Eudragit® does not swell at about pH<6.5 and is soluble at about pH>7. Eudragit RL and Eudragit RS are water swellable, and the amount of water absorbed by these polymers is pH-dependent; however, dosage forms coated with Eudragit RL and RS are pH-independent.

In certain preferred embodiments, the acrylic coating comprises a mixture of two acrylic resin lacquers commercially available from Rohm under the Tradenames Eudragit® RL30D and Eudragit® RS30D, respectively. Eudragit® RL300 and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a sustained-release formulation having a desirable dissolution profile. Desirable sustained-release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L. In embodiments of the present invention where the coating comprises an aqueous dispersion of a hydrophobic sustained release material, the inclusion of an effective amount of a plasticizer in the aqueous dispersion of hydrophobic material will further improve the physical properties of the sustained-release coating. For example, because ethylcellulose has a relatively high glass transition temperature and does not form flexible films under normal coating conditions, it is preferable to incorporate a plasticizer into an ethylcellulose coating containing sustained-release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

In certain embodiments, the uncoated/coated sustained release spheroids, granules, or matrix multiparticulates containing the opioid analgesic; and one or more aversive agents; are cured until an endpoint is reached at which the sustained release spheroids, granules, or matrix multiparticulates provide a stable dissolution of the opioid. The curing endpoint may be determined by comparing the dissolution profile (curve) of the dosage form immediately after curing to the dissolution profile (curve) of the dosage form after exposure to accelerated storage conditions of, e.g., at least one month at a temperature of 40° C. and a relative humidity of 75%. Cured formulations are described in detail in U.S. Pat. Nos. 5,273,760; 5,286,493; 5,500,227; 5,580,578; 5,639,476; 5,681,585; and 6,024,982. Other examples of sustained-release formulations and coatings which may be used in accordance with the present invention include those described in U.S. Pat. Nos. 5,324,351; 5,356,467; and 5,472,712.

In addition to the above ingredients, the spheroids, granules, or matrix multiparticulates may also contain suitable quantities of other materials, e.g., diluents, lubricants, binders, granulating aids, and glidants that are conventional in the pharmaceutical art in amounts up to about 50% by weight of the formulation if desired. The quantities of these additional materials will be sufficient to provide the desired effect to the desired formulation.

Specific examples of pharmaceutically acceptable carriers and excipients that may be used to formulate oral dosage forms are described in the *Handbook of Pharmaceutical Excipients*, American Pharmaceutical Association (1986), incorporated by reference herein.

It has further been found that the addition of a small amount of talc to the sustained release coating reduces the tendency of the aqueous dispersion to stick during processing, and acts as a polishing agent.

Osmotic Dosage Forms

Sustained release dosage forms according to the present invention may also be prepared as osmotic dosage formulations. The osmotic dosage forms preferably include a bilayer core comprising a drug layer (containing the opioid analgesic and optionally one or more aversive agents) and a delivery or push layer (which may contain the one or more aversive agents), wherein the bilayer core is surrounded by a semipermeable wall and optionally having at least one passageway disposed therein.

The expression "passageway" as used for the purpose of this invention, includes aperture, orifice, bore, pore, porous element through which the opioid analgesic can be pumped, diffuse or migrate through a fiber, capillary tube, porous overlay, porous insert, microporous member, or porous composition. The passageway can also include a compound that erodes or is leached from the wall in the fluid environment of use to produce at least one passageway. Representative compounds for forming a passageway include erodible poly(glycolic) acid, or poly(lactic) acid in the wall; a gelatinous filament; a water-removable poly(vinyl alcohol); leachable compounds such as fluid-removable pore-forming polysaccharides, acids, salts or oxides. A passageway can be formed by leaching a compound from the wall, such as sorbitol, sucrose, lactose, maltose, or fructose, to form a sustained-release dimensional pore-passageway. The passageway can have any shape, such as round, triangular, square and elliptical, for assisting in the sustained metered release of opioid analgesic from the dosage form. The dosage form can be manufactured with one or more passageways in spaced-apart relation on one or more surfaces of the dosage form. A passageway and equipment for forming a passageway are described in U.S. Pat. Nos. 3,845,770; 3,916,899; 4,063,064 and 4,088,864. Passageways comprising sustained-release dimensions sized, shaped and adapted as a releasing-pore formed by aqueous leaching to provide a releasing-pore of a sustained-release rate are described in U.S. Pat. Nos. 4,200,098 and 4,285,987.

In certain embodiments, the bilayer core comprises a drug layer with opioid analgesic and a displacement or push layer optionally containing the one or more aversive agents. The one or more aversive agents may optionally be included in the drug layer instead of or in addition to being included in the push layer. In certain embodiments the drug layer may also comprise at least one polymer hydrogel. The polymer hydrogel may have an average molecular weight of between about 500 and about 6,000,000. Examples of polymer hydrogels include but are not limited to a maltodextrin polymer comprising the formula $(C_6H_{12}O_5)_n \cdot H_2O$, wherein n is 3 to 7,500, and the maltodextrin polymer comprises a 500 to 1,250,000 number-average molecular weight; a poly(alkylene oxide) represented by, e.g., a poly(ethylene oxide) and a poly(propylene oxide) having a 50,000 to 750,000 weight-average molecular weight, and more specifically represented by a poly(ethylene oxide) of at least one of 100,000, 200,000, 300,000 or 400,000 weight-average molecular weights; an alkali carboxyalkylcellulose, wherein the alkali is sodium or potassium, the alkyl is methyl, ethyl, propyl, or butyl of 10,000 to 175,000 weight-average molecular weight; and a copolymer of ethylene-acrylic acid, including methacrylic and ethacrylic acid of 10,000 to 500,000 number-average molecular weight.

In certain embodiments of the present invention, the delivery or push layer comprises an osmopolymer. Examples of an osmopolymer include but are not limited to a member selected from the group consisting of a polyalkylene oxide and a carboxyalkylcellulose. The polyalkylene oxide possesses a 1,000,000 to 10,000,000 weight-average molecular weight. The polyalkylene oxide may be a member selected from the group consisting of polymethylene oxide, polyethylene oxide, polypropylene oxide, polyethylene oxide having a 1,000,000 average molecular weight, polyethylene oxide comprising a 5,000,000 average molecular weight, polyethylene oxide comprising a 7,000,000 average molecular weight, cross-linked polymethylene oxide possessing a 1,000,000 average molecular weight, and polypropylene oxide of 1,200,000 average molecular weight. Typical osmopolymer carboxyalkylcellulose comprises a member selected from the group consisting of alkali carboxyalkylcellulose, sodium carboxymethylcellulose, potassium carboxymethylcellulose, sodium carboxyethylcellulose, lithium carboxymethylcellulose, sodium carboxyethylcellulose, carboxyalkylhydroxyalkylcellulose, carboxymethylhydroxyethyl cellulose, carboxyethylhydroxyethylcellulose and carboxymethylhydroxypropylcellulose. The osmopolymers used for the displacement layer exhibit an osmotic pressure gradient across the semipermeable wall. The osmopolymers imbibe fluid into dosage form, thereby swelling and expanding as an osmotic hydrogel (also known as osmogel), whereby they push the contents of the drug layer from the osmotic dosage form.

The push layer may also include one or more osmotically effective compounds also known as osmagents and as osmotically effective solutes. They imbibe an environmental fluid, for example, from the gastrointestinal tract, into dosage form and contribute to the delivery kinetics of the displacement layer. Examples of osmotically active compounds comprise a member selected from the group consisting of osmotic salts and osmotic carbohydrates. Examples of specific osmagents include but are not limited to sodium chloride, potassium chloride, magnesium sulfate, lithium phosphate, lithium chloride, sodium phosphate, potassium sulfate, sodium sulfate, potassium phosphate, glucose, fructose and maltose.

The push layer may optionally include a hydroxypropylalkylcellulose possessing a 9,000 to 450,000 number-average molecular weight. The hydroxypropylalkylcellulose is represented by a member selected from the group consisting of hydroxypropylmethylcellulose, hydroxypropylethylcellulose, hydroxypropyl isopropyl cellulose, hydroxypropylbutylcellulose, and hydroxypropylpentylcellulose.

The push layer may also optionally comprise an antioxidant to inhibit the oxidation of ingredients. Some examples of antioxidants include but are not limited to a member selected from the group consisting of ascorbic acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiary butylphenol, alphatocopherol, and propylgallate.

In certain alternative embodiments, the dosage form comprises a substantially homogenous core comprising opioid analgesic, one or more aversive agents, a pharmaceutically acceptable polymer (e.g., polyethylene oxide), optionally a disintegrant (e.g., polyvinylpyrrolidone), optionally an absorption enhancer (e.g., a fatty acid, a surfactant, a chelating agent, a bile salt, etc.). The substantially homogenous core is surrounded by a semipermeable wall having a passageway (as defined above) for the release of the opioid analgesic, and the one or more aversive agents.

In certain embodiments, the semipermeable wall comprises a member selected from the group consisting of a cellulose ester polymer, a cellulose ether polymer and a cellulose ester-ether polymer. Representative wall polymers comprise a member selected from the group consisting of cellulose acylate, cellulose diacylate, cellulose triacylate, cellulose acetate, cellulose diacetate, cellulose triacetate, mono-, di- and tricellulose alkenylates, and mono-, di- and tricellulose alkinylates. The poly(cellulose) used for the Present invention comprises a number-average molecular weight of 20,000 to 7,500,000.

Additional semipermeable polymers for the purpose of this invention comprise acetaldehyde dimethycellulose acetate, cellulose acetate ethylcarbamate, cellulose acetate methylcarbamate, cellulose diacetate, propylcarbamate, cellulose acetate diethylaminoacetate; semipermeable polyamide; semipermeable polyurethane; semipermeable sulfonated polystyrene; semipermeable cross-linked polymer formed by the coprecipitation of a polyanion and a polycation as disclosed in U.S. Pat. Nos. 3,173,876; 3,276,586; 3,541,005; 3,541,006 and 3,546,876; semipermeable polymers as disclosed by Loeb and Sourirajan in U.S. Pat. No. 3,133,132; semipermeable crosslinked polystyrenes; semipermeable cross-linked poly(sodium styrene sulfonate); semipermeable crosslinked poly(vinylbenzyltrimethyl ammonium chloride); and semipermeable polymers possessing a fluid permeability of $2.5 \times 10^{-8}$ to $2.5 \times 10^{-2}$ (cm·sup.2/hr·atm) expressed per atmosphere of hydrostatic or osmotic pressure difference across the semipermeable wall. Other polymers useful in the present invention are known in the art in U.S. Pat. Nos. 3,845,770; 3,916,899 and 4,160,020; and in Handbook of Common Polymers, Scott, J. R. and W. J. Roff, 1971, CRC Press, Cleveland, Ohio.

In certain embodiments, preferably the semipermeable wall is nontoxic, inert, and it maintains its physical and chemical integrity during the dispensing life of the drug. In certain embodiments, the dosage form comprises a binder. An example of a binder includes, but is not limited to a therapeutically acceptable vinyl polymer having a 5,000 to 350,000 viscosity-average molecular weight, represented by a member selected from the group consisting of poly-n-vinylamide, poly-n-vinylacetamide, poly(vinyl pyrrolidone), also known as poly-n-vinylpyrrolidone, poly-n-vinylcaprolactone, poly-n-vinyl-5-methyl-2-pyrrolidone, and poly-n-vinyl-pyrrolidone copolymers with a member selected from the group consisting of vinyl acetate, vinyl alcohol, vinyl chloride, vinyl fluoride, vinyl butyrate, vinyl laureate, and vinyl stearate. Other binders include for example, acacia, starch, gelatin, and hydroxypropylalkylcellulose of 9,200 to 250,000 average molecular weight.

In certain embodiments, the dosage form comprises a lubricant, which may be used during the manufacture of the dosage form to prevent sticking to die wall or punch faces. Examples of lubricants include but are not limited to magnesium stearate, sodium stearate, stearic acid, calcium stearate, magnesium oleate, oleic acid, potassium oleate, caprylic acid, sodium stearyl fumarate, and magnesium palmitate.

Transdermal Delivery Systems

The formulations of the present invention may be formulated as a transdermal delivery system, such as transdermal patches. In certain embodiments of the present invention, a transdermal patch comprises an opioid agonist contained in a reservoir or a matrix, and an adhesive which allows the transdermal device to adhere to the skin, allowing the passage of the active agent from the transdermal device through the skin of the patient, with the inclusion of the aversive agents as disclosed herein which are not releasable when the dosage form is administered intact but which are releasable when the dosage form is broken or tampered with in order to release the opioid from the transdermal system.

Transdermal delivery system providing a controlled-release of an opioid agonist is known. For example, Duragesic® patch (commercially available from Janssen Pharmaceutical) contains an opioid agonist (fentanyl) and is said to provide adequate analgesia for up to 48 to 72 hours (2 to 3 days). This formulation can be reformulated with an aversive agent as disclosed herein.

There are several types of transdermal formulations of buprenorphine reported in the literature. See, for example, U.S. Pat. No. 5,240,711 (Hille et al.), U.S. Pat. No. 5,225,199 (Hidaka et al.), U.S. Pat. No. 5,069,909 (Sharma et al.), U.S. Pat. No. 4,806,341 (Chien et al.), and U.S. Pat. No. 5,026,556 (Drust et al.), all of which are hereby incorporated by reference. These transdermal devices can also be reformulated with the aversive agents as disclosed herein.

The transdermal delivery system used in the present invention may also be prepared in accordance with U.S. Pat. No. 5,069,909 (Sharma et al.), hereby incorporated by reference. This patent describes a laminated composite for administering buprenorphine transdermally to treat pain. The transdermal delivery system used in the present invention may also be prepared in accordance with U.S. Pat. No. 4,806,341 (Chien et al.), hereby incorporated by reference. This patent describes a transdermal morphinan narcotic analgesic or antagonist (including buprenorphine) pharmaceutical polymer matrix dosage unit having a backing layer which is substantially impervious to the buprenorphine, and a polymer matrix disc layer which is adhered to the backing layer and which has microdispesed therein effective dosage amounts of the buprenorphine.

The transdermal delivery system used in the present invention may also be that described in U.S. Pat. No. 5,026,556 (Drust et al.), hereby incorporated by reference. Therein, compositions for the transdermal delivery of buprenorphine comprise buprenorphine in a carrier of a polar solvent material selected from the group consisting of $C_3$-$C_4$ diols, $C_3$-$C_6$ triols, and mixtures thereof, and a polar lipid material selected from the group consisting of fatty alcohol esters, fatty acid esters, and mixtures thereof; wherein the polar solvent material and the lipid material are present in a weight ratio of solvent material:lipid material of from 60:40 to about 99:1. The transdermal delivery system used in the present invention may also be that described in U.S. Pat. No. 4,588,580 (Gale, et al.), hereby incorporated by reference. That system comprises a reservoir for the drug having a skin proximal, material releasing surface area in the range of about 5-100 $cm^2$ and containing between 0.1 and 50% by weight of a skin permeable form of the buprenorphine. The reservoir contains an aqueous gel comprising up to about 47-95% ethanol, 1-10% gelling agent, 0.1-10% buprenorphine, and release rate controlling means disposed in the flow path of the drug to the skin which limits the flux of the buprenorphine from the system through the skin.

The transdermal delivery system used in the present invention may also be that described in PCT/US01/04347 to Oshlack et al.

The present invention is contemplated to encompass all transdermal formulations, e.g., the technologies described above, with the inclusion of an aversive agent, such that the dosage form deters abuse of the opioid therein.

The aversive agent in non-releasable form when administered intact can be formulated in accordance with U.S. Pat. No. 5,149,538 to Granger, hereby incorporated by reference. Alternatively, the aversive agent and the opioid agonist can be separated from the opioid by a layer which becomes disrupted when the dosage form is tampered with, thereby mixing the aversive agent with the opioid agonist. Alternatively, a combination of both systems can be used.

Suppositories

The controlled release formulations of the present invention may be formulated as a pharmaceutical suppository for rectal administration comprising an opioid analgesic, and at least one aversive agent in a controlled release matrix, and a suppository vehicle (base). Preparation of controlled release suppository formulations is described in, e.g., U.S. Pat. No. 5,215,758.

The suppository base chosen should be compatible with the agent(s) of the present invention. Further, the suppository base is preferably non-toxic and nonirritating to mucous membranes, melts or dissolves in rectal fluids, and is stable during storage.

In certain preferred embodiments of the present invention for both water-soluble and water-insoluble drugs, the suppository base comprises a fatty acid wax selected from the group consisting of mono-, di- and triglycerides of saturated, natural fatty acids of the chain length $C_{12}$ to $C_{18}$.

In preparing the suppositories of the present invention other excipients may be used. For example, a wax may be used to form the proper shape for administration via the rectal route. This system can also be used without wax, but with the addition of diluent filled in a gelatin capsule for both rectal and oral administration.

Examples of suitable commercially available mono-, di- and triglycerides include saturated natural fatty acids of the 12-18 carbon atom chain sold under the trade name Novata™ (types AB, AB, B, BC, BD, BBC, E, BCF, C, D and 299), manufactured by Henkel, and Witepsol™ (types H5, H12, H15, H175, H185, H19, H32, H35, H39, H42, W25, W31, W35, W45, S55, S58, E75, E76 and E85), manufactured by Dynamit Nobel.

Other pharmaceutically acceptable suppository bases may be substituted in whole or in part for the above-mentioned mono-, di- and triglycerides. The amount of base in the suppository is determined by the size (i.e. actual weight) of the dosage form, the amount of base (e.g., alginate) and drug used. Generally, the amount of suppository base is from about 20 percent to about 90 percent by weight of the total weight of the suppository. Preferably, the amount of base in the suppository is from about 65 percent to about 80 percent, by weight of the total weight of the suppository.

In certain embodiments of the dosage forms of the present invention may also include a surfactant. Surfactants useful in accordance with the present invention, include for example, ionic and nonionic surfactants or wetting agents commonly used in the formulation of pharmaceuticals, including but not limited to castor oil derivatives, cholesterol, polyglycolyzed glycerides, acetylated monoglycerides, sorbitan fatty acid esters, poloxamers, polysorbates, polyoxyethylene sorbitan fatty acid esters, polyoxyethylene compounds, monoglycerides or ethoxylated derivatives thereof, diglycerides or polyoxyethylene derivatives thereof, sodium docusate, sodium laurylsulfate, cholic acid or derivatives thereof, ethoxylated alcohols, ethoxylated esters, ethoxylated amides, polyoxypropylene compounds, propoxylated alcohols, ethoxylated/propoxylated block polymers, propoxylated esters, alkanolamides, amine oxides, fatty acid esters of polyhydric alcohols, ethylene glycol esters, diethylene glycol esters, propylene glycol esters, glycerol esters, polyglycerol fatty acid esters, SPAN's (e.g., sorbitan esters), TWEEN's (i.e., sucrose esters), glucose (dextrose) esters, alkali metal sulfates, quaternary ammonium compounds, amidoamines, and aminimides, simethicone, lecithins, alcohols, phospholipids, and mixtures thereof.

Mixed surfactant/wetting agents useful in accordance with the present invention include, for example, sodium lauryl sulfate/polyethylene glycol (PEG) 6000 and sodium lauryl sulfate/PEG 6000/stearic acid, etc.

In certain embodiments of the present invention, the dosage form may also include an emulsifying agent. Emulsifying agents useful in accordance with the present invention include, for example, monoglycerides, sucrose/fatty acid esters, polyglycerol/fatty acid esters, sorbitan/fatty acid esters, lecithins, potassium and sodium salts of rosin acids and higher fatty acids, as well as sulfates and sulfonates of these acids, amine salts of hydroxylamines of long-chain fatty acid esters, quaternary ammonium salts such as stearyl-dimethylbenzylammonium chloride and tridecylbenzenehydroxyethylimidazole chloride, phosphoric esters of higher alcohols such as capryl and octyl alcohol, and monoesters of oleic acid and pentaerythritol such as sorbitan monooleates, and mixtures thereof.

The oral dosage form and methods for use of the present invention may further include, in addition to an opioid analgesic and at least one aversive agent, one or more drugs that may or may not act synergistically with the opioid analgesic. Thus, in certain embodiments, a combination of two opioid analgesics may be included in the dosage form. For example, the dosage form may include two opioid analgesics having different properties, such as half-life, solubility, potency, and a combination of any of the foregoing.

In yet further embodiments, one or more opioid analgesic is included and a further non-opioid drug is also included. Such non-opioid drugs would preferably provide additional analgesia, and include, for example, aspirin, acetaminophen; non-steroidal anti-inflammatory drugs ("NSAIDS"), e.g., ibuprofen, ketoprofen, etc.; N-methyl-D-aspartate (NMDA) receptor antagonists, e.g., a morphinan such as dextromethorphan or dextrorphan, or ketamine; cyclooxygenase-II inhibitors ("COX-II inhibitors"); and/or glycine receptor antagonists.

In certain preferred embodiments of the present invention, the invention allows for the use of lower doses of the opioid analgesic by virtue of the inclusion of an additional non-opioid analgesic, such as an NSAID or a COX-2 inhibitor. By using lower amounts of either or both drugs, the side effects associated with effective pain management in humans are reduced.

Suitable non-steroidal anti-inflammatory agents, including ibuprofen, diclofenac, naproxen, benoxaprofen, flurbiprofen, fenoprofen, flubufen, ketoprofen, indoprofen, piro-profen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidornetacin, acemetacin, fentiazac, clidanac, oxipinac, mefenamic acid, meclofenamic acid, flufenamic acid, niflumic acid, tolfenamic acid, diflurisal, flufenisal, piroxicam, sudoxicam or isoxicam, and the like. Useful dosages of these drugs are well known to those skilled in the art.

N-methyl-D-aspartate (NMDA) receptor antagonists are well known in the art, and encompass, for example, morphinans such as dextromethorphan or dextrorphan, ketamine, or pharmaceutically acceptable salts thereof. For purposes of the present invention, the term "NMDA antagonist" is also deemed to encompass drugs that block a major intracellular consequence of NMDA-receptor activation, e.g. a ganglioside such as $GM_1$ or $GT_{1b}$, a phenothiazine such as trifluoperazine or a naphthalenesulfonamide such as N-(6-aminohexyl)-5-chloro-1-naphthalenesulfonamide. These drugs are stated to inhibit the development of tolerance to and/or dependence on addictive drugs, e.g., narcotic analgesics such as morphine, codeine, etc. in U.S. Pat. Nos. 5,321,012 and 5,556,838 (both to Mayer, et al.), and to treat chronic pain in U.S. Pat. No. 5,502,058 (Mayer, et al.), all of which are hereby incorporated by reference. The NMDA antagonist may be included alone, or in combination with a local anesthetic such as lidocaine, as described in these Mayer, et. al. patents.

The treatment of chronic pain via the use of glycine receptor antagonists and the identification of such drugs is described in U.S. Pat. No. 5,514,680 (Weber, et al.).

COX-2 inhibitors have been reported in the art and many chemical structures are known to produce inhibition of cyclooxygenase-2. COX-2 inhibitors are described, for example, in U.S. Pat. Nos. 5,616,601; 5,604,260; 5,593,994; 5,550,142; 5,536,752; 5,521,213; 5,474,995; 5,639,780; 5,604,253; 5,552,422; 5,510,368; 5,436,265; 5,409,944; and 5,130,311, all of which are hereby incorporated by reference. Certain preferred COX-2 inhibitors include celecoxib (SC-58635), DUP-697, flosulide (CGP-28238), meloxicam, 6-methoxy-2 naphthylacetic acid (6-MNA), MK-966 (also known as Vioxx), nabumetone (prodrug for 6-MNA), nimesulide, NS-398, SC-5766, SC-58215, T-614; or combinations thereof. Dosage levels of COX-2 inhibitor on the order of from about 0.005 mg to about 140 mg per kilogram of body weight per clay are therapeutically effective in combination with an opioid analgesic. Alternatively, about 0.25 mg to about 7 g per patient per day of a COX-2 inhibitor is administered in combination with an opioid analgesic.

In yet further embodiments, a non-opioid drug can be included which provides a desired effect other than analgesia, e.g., antitussive, expectorant, decongestant, antihistamine drugs, local anesthetics, and the like.

The invention disclosed herein is meant to encompass the use of any pharmaceutically acceptable salts thereof of the disclosed opioid analgesics. The pharmaceutically acceptable salts include, but are not limited to, metal salts such as sodium salt, potassium salt, secium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, aspartginate, glutamate and the like.

Some of the opioid analgesics disclosed herein may contain one or more asymmetric centers and may thus give rise to enantiomers, diastereomers, and other stereoisomeric forms. The present invention is also meant to encompass the use of any such possible forms as well as their racemic and resolved forms and mixtures thereof. When the compounds described herein contain olefinic double bonds or other centers of geometric asymmetry, and unless specified otherwise, it is intended to include both E and Z geometric isomers. The use of all tautomers are intended to be encompassed by the present invention as well.

The oral dosage forms of the present invention may be in the form of tablets, troches, lozenges, powders or granules, hard or soft capsules, microparticles (e.g., microcapsules, microspheres and the like), buccal tablets, etc.

In certain embodiments, the present invention provides for a method of preventing abuse of an oral controlled release dosage form of an opioid analgesic comprising preparing the dosage forms as described above.

In certain embodiments, the present invention provides for a method of preventing diversion of an oral controlled release dosage form of an opioid analgesic comprising preparing the dosage forms as described above.

In certain embodiments, the present invention provides for a method of treating pain while at the same time reducing the risk of abuse by administering to a human patient the dosage forms described above.

As previously disclosed, the aversive agents of the present invention can be used for other drugs which can be the subject of abuse. Opioids, e.g., oxycodone are the preferred embodiments of the invention. However, it is contemplated that all of the disclosure herein With respect to opioid formulations containing the aversive agent(s) can be applied to formulations containing drugs of abuse other than opioids.

The following examples illustrate various aspects of the present invention. They are not to be construed to limit the claims in any manner whatsoever.

Example 1

A 20 mg Oxycodone Formulation was Prepared Containing Xanthan Gum as the Aversive Agent In this example, a small amount of xanthan gum is added to the oxycodone formulation during the granulation process. Other gelling agents such as curdlan, carrageenan, alginates, pectin, gelatin, furcelleran, agar, guar locust bean gum, tara gum, tragacanth, acacia, glucomannans, karaya, starch and starch derivatives, egg white powder, lacto albumin, soy protein, Jargel, gellan gum, welan gum, rhamsan gum, and the like, could also be used as gelling agents. Other semi-synthetic materials such as chitosan, pullulan, polylaevulan, hydroxypropyl cellulose, methylcellulose, hydroxypropylmethyl cellulose, carboxymethyl cellulose ethylhydroxyethyl cellulose, all ether derivatives of cellulose, and the like, could also be used as alternate gelling materials.

TABLE 1

| Ingredients | Amt/Unit (mg) | Amount/Batch (gm) |
|---|---|---|
| Oxycodone HCl | 20.0 | 209.6* |
| Spray Dried Lactose | 59.25 | 592.5 |
| Povidone | 5.0 | 50.0 |
| Eudragit RS30D (solids) | 10.0 | 100 |
| Triacetin | 2.0 | 20.0 |
| Xanthan gum | 9.0 | 90.0 |
| Stearyl Alcohol | 25.0 | 250.0 |
| Talc | 2.5 | 25.0 |
| Magnesium Stearate | 1.25 | 12.5 |
| Opadry Pink Y-S-14518A | 5.0 | 50.0 |

*adjusted for 99.6% assay and 4.2% residual moisture.

Process
1. Dispersion: Disperse Eudragit and Triacetin in an aqueous medium to form a Eudragit/Triacetin dispersion.
2. Granulation: Spray the Eudragit/Triacetin dispersion onto the oxycodone HCl, Spray Dried Lactose, xanthan gum and Povidone using a fluid bed granulator.
3. Milling: Discharge the granulation and pass through a mill.
4. Waxing: Melt the stearyl alcohol and add to the milled granulation using a mixer. Allow to cool.
5. Milling: Pass the cooled granulation through a mill.
6. Lubrication: Lubricate the granulation with talc and magnesium stearate using a mixer.
7. Compression: Compress the granulation into tablets using a tablet press.

Example 2

A 40 mg Oxycodone Formulation was Prepared Containing Xanthan Gum as the Aversive Agent To determine the effect of varying amount of xanthan gum on the gelling property and dissolution rate of an oxycodone tablet, three levels of xanthan gum were added to 40 mg oxycodone granulation and compressed into tablets. Oxycodone recovery from water extraction of the tablet and the drug release rate was determined. The oxycodone granulation formulation of Example 2 is listed in Table 2 below.

TABLE 2

| Ingredients | Amt/Unit (mg) |
|---|---|
| Oxycodone HCl | 40.0 |
| Spray Dried Lactose | 39.25 |
| Povidone | 5.0 |
| Eudragit RS30D (solids) | 10.0 |
| Triacetin | 2.0 |
| Stearyl Alcohol | 25.0 |
| Talc | 2.5 |
| Magnesium Stearate | 1.25 |
| Total | 125 |

Example 2A to 2C were prepared adding different amounts (3 mg, 5 mg, and 9 mg) of xanthan gum to a 125 mg oxycodone granulation of Example 2.

Example 2A

| Ingredients | Amt/Unit (mg) |
|---|---|
| Oxycodone granulation | 125 |
| Xanthan gum | 3 |
| Total | 128 |

Example 2B

| Ingredients | Amt/Unit (mg) |
|---|---|
| Oxycodone granulation | 125 |
| Xanthan gum | 5 |
| Total | 130 |

Example 2C

| Ingredients | Amt/Unit (mg) |
|---|---|
| Oxycodone granulation | 125 |
| Xanthan gum | 9 |
| Total | 134 |

Process

1. Dispersion: Disperse Eudragit and Triacetin in an aqueous medium to form an Eudragit/Tracetin dispersion.
2. Granulation: Spray the Eudragit/Triacetin dispersion onto the Oxycodone HCl, Spray Dried Lactose and Povidone using a fluid bed granulator.
3. Milling: Discharge the granulation and pass through a mill.
4. Waxing: Melt the stearyl alcohol and add to the milled granulation using a mixer. Allow to cool.
5. Milling: Pass the cooled granulation through a mill.
6. Lubrication: Lubricate the granulation with talc and magnesium stearate using a mixer.
7. Add xanthan gum (3 levels) to the granulation and mix well.
8. Compression: Compress the granulation into tablets using a tablet press.

Example 3

A thickening agent, citrus pectin, was added to a placebo Oxycontin® 10 mg tablet (tablet without the drug present) and small amounts of water (e.g., 1 ml, 2 ml, and 3 ml) were added. The following results were obtained and compared and listed in Table 3:

TABLE 3

Formation of gel at different concentrations
(Water, pectin and Oxycontin ® 10 mg placebo Tablet)

| Weight of Pectin (mg) | Extraction Volume (1 ml) | Extraction Volume (2 ml) | Extraction Volume (3 ml) |
|---|---|---|---|
| 25 | THICK (55 cP) | THICK (34 cP) | THICK (24 cP) |
| 50 | THICKEST (375 cP) | THICKER (84 cP) | THICK (42 cP) |
| 75 | THICKEST (1830 cP) | THICKEST (154 cP) | THICKER (94 cP) |

THIN (less than 10 cP): The solution can be filled into a syringe
THICK (10 cP to 60 cP): Although a syringe can be filled with this solution, it was hard to do.
THICKER (60 cP to 120 cP): Syringe cannot be filled without picking up large pockets of air.
THICKEST (120 cP or greater, e.g., up to 2000 cP or up to 5000 cP): The solution cannot be injected or is very difficult to draw into a syringe or to inject.

The results summarized in Table 3 indicate that all the extracts were hard or difficult to pull into an insulin syringe. The pectin can also emulsify the excipients in the aqueous mixture making their filtration difficult. The tablet's coating is suspended in the mixture resembling a paste. All the samples have a creamy texture and milk like color. Additionally, the filtration with cotton cannot remove the suspended material, thus the mixture would not appeal to an addict.

This experiment shows that an ingredient, such as pectin, could be added to the Oxycontin® Tablets to make the extraction of the oxycodone more difficult and thus reducing the potential for abuse. Addition of pectin to the tablets appears to make the extraction extremely difficult.

Example 4

In Example 4, controlled release tablets containing an opioid agonist (oxycodone HCl) and gelling agent (microcrystalline cellulose) are prepared. The controlled release tablets comprise granulates comprising the opioid agonist and the gelling agent dispersed in a controlled release matrix. The granulates are combined with melted wax (stearyl alcohol) to produce waxed granulates, which are then milled and mixed with other excipients and compressed into tablets.

TABLE 4

| Ingredient | Amt/unit (mg) | Amt/batch (kg) |
|---|---|---|
| Oxycodone HCl | 10.00 | 11.00 |
| Microcrystalline Cellulose | 200.00 | 220.00 |
| Spray Dried Lactose | 68.75 | 75.62 |
| Povidone | 5.00 | 5.50 |
| Triacetin | 2.00 | 2.20 |
| Stearyl Alcohol | 25.00 | 27.50 |
| Talc | 2.50 | 2.75 |
| Magnesium Stearate | 1.25 | 1.38 |
| Opadry White | 5.00 | 5.50 |
| Purified Water | | 31.16* |
| Total | 319.50 | 382.61 |

*Remains in product as residual moisture only.

Process:
1. Granulation Place Oxycodone HCl, Spray Dried Lactose, water, Povidone, Microcrystalline Cellulose, and Triacetin into a fluid bed granulator.
2. Milling Pass the granulation through a rotating impeller mill.
3. Drying Dry granulation if moisture content is too high.
4. Waxing Melt Stearyl Alcohol and wax the above granulation by adding melted Stearyl Alcohol onto granulation while mixing.
5. Cooling Cool the waxed granulation in a fluid bed dryer.
6. Milling Pass the cooled waxed granulation through a rotating impeller mill.
7. Blending Blend the milled waxed granulation, Talc and Magnesium Stearate.
8. Compression Compress the resultant granulation using a tablet press.
9. Coating Prepare a film coating solution by dispersing the Opadry in Purified Water and applying it to the tablet cores.

Example 5

In Example 5, controlled release tablets containing a opioid agonist (morphine sulfate) and gelling agent (hydroxyethyl cellulose) are prepared. The controlled release tablets comprise granulates comprising the opioid agonist and the gelling agent in a controlled-release matrix. The granulates are combined with melted wax (cetostearyl alcohol) to produce waxed granulates, which are then milled and mixed with other excipients and compressed into tablets.

TABLE 5

| Ingredient | Amt/unit (mg) | Amt/batch (kg) |
|---|---|---|
| Morphine Sulfate (pentahydrate) | 30.00 | 108.0 |
| Spray Dried Lactose | 69.5 | 250.2 |
| Hydroxyethyl Cellulose | 600.0 | 2160.0 |
| Purified Water | | 75.9* |
| Cetostearyl Alcohol | 35.0 | 126.0 |
| Talc | 3.0 | 10.8 |

TABLE 5-continued

| Ingredient | Amt/unit (mg) | Amt/batch (kg) |
|---|---|---|
| Magnesium Stearate | 2.0 | 7.2 |
| Opadry Purple | 3.0 | 10.8 |
| Purified Water | | 61.2* |
| Total | 742.50 | 2673 |

*Remains in product as residual moisture only.

Process:
1. Granulation Place Morphine Sulfate, Spray Dried Lactose, water, and Hydroxyethyl Cellulose in a mixer and granulate.
2. Drying Dry the above granulation in a fluid bed dryer.
3. Milling Pass the granulation through a mill.
4. Drying Dry granulation if moisture content is too high.
5. Waxing Melt Cetostearyl Alcohol and wax the above granulation by adding melted Cetostearyl Alcohol onto granulation while mixing.
6. Cooling Cool the waxed granulation in a fluid bed dryer.
7. Milling Pass the cooled waxed granulation through a mill.
8. Blending Blend the milled waxed granulation, Talc and Magnesium Stearate.
9. Compression Compress the resultant granulation using a tablet press.
10. Coating Prepare a film coating solution by dispersing the Opadry in Purified Water and applying it to the tablet cores.

In Examples 6-8, 10 mg oxycodone HCL tablets are prepared as follows:

Example 6

A controlled release tablet having the formula listed below is prepared by wet granulating oxycodone hydrochloride (25.00 gm) with lactose monohydrate (417.5 gm), and hydroxyethyl cellulose (100.00 gm). The granules are sieved through a 12 mesh screen. The granules are then dried in a fluid bed dryer at 50E C and sieved through a 16 mesh screen.

Molten cetostearyl alcohol (300.0 gm) is added to the warmed oxycodone containing granules, and the whole was mixed thoroughly. The mixture is allowed to cool in the air, regranulated and sieved through a 16 mesh screen.

Purified Talc (15.0 gm), magnesium stearate (7.5 gm), and pectin (62.5 gm) are then added and mixed with the granules. The granules are then compressed into tablets.

TABLE 6

| Ingredient | Amt/unit (mg) | Amt/batch (g) |
|---|---|---|
| Oxycodone HCl | 10.00 | 25.0 |
| Lactose Monohydrate | 167.00 | 417.5 |
| Hydroxyethylcellulose | 40.00 | 100.0 |
| Cetostearyl alcohol | 120.00 | 300.0 |
| Talc | 6.0 | 15.0 |
| Magnesium Stearate | 3.0 | 7.5 |
| Pectin | 25.00 | 62.5 |

Example 7

A controlled release tablet containing 10 mg of oxycodone and 50.00 mg of pectin and having the following formula is prepared in the same manner as in Example 6:

TABLE 7

| Ingredient | Amt/unit (mg) | Amt/batch (g) |
|---|---|---|
| Oxycodone HCl | 10.00 | 25.0 |
| Lactose Monohydrate | 167.00 | 417.5 |
| Hydroxyethylcellulose | 40.00 | 100.0 |
| Cetostearyl alcohol | 120.00 | 300.0 |
| Talc | 6.0 | 15.0 |
| Magnesium Stearate | 3.0 | 7.5 |
| Pectin | 50.00 | 125.00 |

Example 8

A controlled release tablet containing 10 mg of oxycodone and 75.00 mg of pectin and having the following formula is prepared as in Example 6:

TABLE 8

| Ingredient | Amt/unit (mg) | Amt/batch (g) |
|---|---|---|
| Oxycodone HCl | 10.00 | 25.0 |
| Lactose Monohydrate | 167.00 | 417.5 |
| Hydroxyethylcellulose | 40.00 | 100.0 |
| Cetostearyl alcohol | 120.00 | 300.0 |
| Talc | 6.0 | 15.0 |
| Magnesium Stearate | 3.0 | 7.5 |
| Pectin | 75.00 | 187.5 |

Example 9

A 20 mg Oxycodone Formulation Containing a Bittering Agent is Prepared

In this example, a small amount of denatonium benzoate is added to an oxycodone formulation during the granulation process. The bitter taste would reduce the abuse of oxycodone by oral or intranasal route. The oxycodone formulation of Example 9 is listed in Table 9 below.

TABLE 9

| Ingredients | Amt/Unit (mg) | Amount/Batch (gm) |
|---|---|---|
| Oxycodone HCl | 20.0 | 209.6* |
| Spray Dried Lactose | 59.25 | 592.5 |
| Povidone | 5.0 | 50.0 |
| Eudragit RS30D (solids) | 10.0 | 100 |
| Triacetin | 2.0 | 20.0 |
| Denatonium benzoate | 0.07 | 0.68 |
| Stearyl Alcohol | 25.0 | 250.0 |
| Talc | 2.5 | 25.0 |
| Magnesium Stearate | 1.25 | 12.5 |
| Opadry Pink Y-S-14518A | 5.0 | 50.0 |

*adjusted for 99.6% assay and 4.2% residual moisture.

Process
1. Dispersion: Dissolve denatonium benzoate in water and the solution is added to the Eudragit/Tracetin dispersion.
2. Granulation: Spray the Eudragit/Triacetin dispersion onto the Oxycodone HCl, Spray Dried Lactose and Povidone using a fluid bed granulator.
3. Milling: Discharge the granulation and pass through a mill.
4. Waxing: Melt the stearyl alcohol and add to the milled granulation using a mixer. Allow to cool.
5. Milling: Pass the cooled granulation through a mill.
6. Lubrication: Lubricate the granulation with talc and magnesium stearate using a mixer.
7. Compression: Compress the granulation into tablets using a tablet press.

Example 10

In Example 10, a substantially non-releasable form of a bittering agent (denatonium benzoate) is prepared by coating denatonium benzoate particles with a coating that renders the denatonium benzoate substantially non-releasable. The formula of Example 10 is listed in Table 10 below.

TABLE 10

| Ingredients | Amt/unit (mg) |
|---|---|
| LOADING | |
| denatonium benzoate | 0.07 |
| Sugar Spheres (30/35 mesh) | 50.0 |
| Opadry White Y-5-7068 | 2.5 |
| Purified Water | 42.5* |
| OVERCOATING | |
| Opadry White Y-5-7068 | 3.02 |
| Purified Water | 17.11* |
| NON-RELEASE COATING (FOR RENDERING BITTERING AGENT SUBSTANTIALLY NON-RELEASABLE) | |
| Eudragit RS30D (dry wt.) | 12.10 |
| Triethyl Citrate | 2.42 |
| Talc | 4.84 |
| Purified Water | 49.21* |
| OVERCOATING | |
| Opadry White Y-5-7068 | 4.12 |
| Purified Water | 23.35* |
| Total | 79.07 |

*Remains in product as residual moisture only.

Process:
1. Solution Preparation Dissolve the denatonium benzoate in Purified Water. Once dissolved, add the Opadry White and continue mixing until a homogeneous dispersion is yielded.
2. Loading Apply the above dispersion onto the Sugar Spheres using a fluid bed coating machine.
3. Overcoating Prepare an overcoating solution by dispersing Opadry White in Purified Water. Apply this dispersion over the sugar spheres loaded with denatonium benzoate using a fluid bed coating machine.
4. Retardant Coating Prepare the non-release coating solution by mixing the Eudragit RS30D, Triethyl Citrate, Talc, and Purified Water. Apply this dispersion over the loaded and overcoated sugar spheres using a fluid bed coating machine.
5. Overcoating Prepare a second overcoating solution by dispersing Opadry White in Purified Water. Apply this dispersion over the non-release coated denatonium benzoate spheres using a fluid bed coating machine
6. Curing Cure the spheres at 45° C. for approximately 48 hours.

Example 11

In Example 11, a substantially non-releasable form of a bittering agent (denatonium benzoate) is prepared as denatonium benzoate containing granulates. The granulates are comprised of denatonium benzoate dispersed in a matrix that renders the denatonium benzoate substantially non-releasable. The formula of Example 11 is listed in Table 11 below.

TABLE 11

| Ingredient | Amt/unit (mg) |
| --- | --- |
| Denatonium benzoate | 0.07 |
| Dicalcium Phosphate | 53.0 |
| Poly (DI-Lactide-Co-Glycolide) polymer (PLGA) MW ~100,000 | 12.0 |
| Ethyl Acetate | |
| Total | 65.07 |

*Used as a vehicle for application of PLGA polymer.

Process:
1. Solution Preparation Dissolve PLGA in Ethyl Acetate by mixing.
2. Granulation Place the denatonium benzoate, and Dicalcium Phosphate in a fluid bed coating machine and granulate by spraying the above solution.

Example 12

In Example 12 a substantially non-releasable form of a bittering agent (denatonium benzoate) is prepared as denatonium benzoate extruded pellets. The formula of Table 12 is listed in Table 12 below.

TABLE 12

| Ingredient | Amt/unit (mg) |
| --- | --- |
| Denatonium benzoate | 0.07 |
| Eudragit RSPO | 180.0 |
| Stearyl Alcohol | 55.0 |
| Total | 235.07 |

Process:
1. Milling Pass stearyl alcohol flakes through an impact mill.
2. Blending Mix Denatonium benzoate, Eudragit, and milled Stearyl Alcohol in a twin shell blender.
3. Extrusion Continuously feed the blended material into a twin screw extruder and collect the resultant strands on a conveyor.
4. Cooling Allow the strands to cool on the conveyor.
5. Pelletizing Cut the cooled strands into pellets using a Pelletizer.
6. Screening Screen the pellets and collect desired sieve portion.

Example 13

Controlled Release Oxycodone 20 mg

In Example 17, a sustained release 20 mg oxycodone formulation is prepared having the formulation listed in Table 13 below.

TABLE 13

| Ingredients | Amt/unit (mg) |
| --- | --- |
| Oxycodone HCl | 20.0 |
| Spray Dried Lactose | 59.25 |
| Povidone | 5.0 |
| Eudragit RS30D (solids) | 10.0 |
| Triacetin | 2.0 |
| Stearyl Alcohol | 25.0 |
| Talc | 2.5 |
| Magnesium Stearate | 1.25 |
| Opadry Pink Y-S-14518A | 4.0 |
| Total | 129.0 |

Process:
1. Granulation: Spray the Eudragit/Triacetin dispersion onto the Oxycodone HCl, Spray Dried Lactose and Povidone using a fluid bed granulator.
2. Milling: Discharge the granulation and pass through a mill.
3. Waxing: Melt the stearyl alcohol and add to the milled granulation using a mixer. Allow to cool.
4. Milling: Pass the cooled granulation through a mill.
5. Lubrication: Lubricate the granulation with talc and magnesium stearate using a mixer.
6. Compression: Compress the granulation into tablets using a tablet press.
7. Film coating: Apply an aqueous film coat to the tablets.

One or more aversive agents as described herein can be incorporated into the oxycodone tablets by one skilled in the art. The one or more aversive agents may be in releasable, non-releasable, or substantially non-releasable form or a combination thereof.

Example 14

Controlled Release Hydrocodone

A sustained release hydrocodone formulation is prepared having the formula in Table 14 below.

TABLE 14

| Ingredient | Amt/unit (mg) | Amt/batch (g) |
| --- | --- | --- |
| Hydrocodone Bitartrate | 15.0 | 320.0 |
| Eudragit RSPO | 76.0 | 1520.0 |
| Eudragit RLPO | 4.0 | 80.0 |
| Stearyl Alcohol | 25.0 | 500.0 |
| Total | 120.0 | 2400.0 |

Process:
1. Blend milled Stearyl Alcohol, Eudragit RLPO, Hydrocodone Bitartrate, and Eudragit RSPO using a Hobart Mixer.
2. Extrude the granulation using a Powder Feeder, Melt Extruder (equipped with the 6×1 mm die head), Conveyor, Lasermike, and Pelletizer.
   Powder feed rate—40 g/min; vacuum—~980 mBar
   Conveyor—such that diameter of extrudate is 1 mm
   Pelletizer—such that pellets are cut to 1 mm in length
3. Screen pellets using #16 mesh and #20 mesh screens. Collect material that passes through the #16 mesh screen and is retained on the #20 mesh screen.
4. Fill size #2 clear gelatin capsules with the pellets. Range: NLT (not less than) 114 mg and NMT (not more than) 126 mg.

One or more aversive agents as described herein can be incorporated into a capsule with the hydrocodone pellets, into the hydrocodone pellets, or on the hydrocodone pellets by one skilled in the art. The one or more aversive agents may be in releasable, non-releasable, or substantially non-releasable form or a combination thereof. Preferably, when pellets comprising the aversive agent(s) are incorporated into the capsule they are indistinguishable from the hydrocodone pellets.

Example 15

Oxycodone HCl Beads for Capsule (Lot #814-40)

A sustained release oxycodone HCl bead formulation is prepared having the formula in Table 15 below.

TABLE 15

| | Ingredients | Amt/unit* (mg) |
|---|---|---|
| Step 1. Drug layering | Oxycodone HCl | 10.5 |
| | Non-pareil beads (30/35 mesh) | 45.349 |
| | Opadry Clear | 2.5 |
| Step 2. Sustained release coat | Eudragit RS30D (dry) | 7.206 |
| | Eudragit RL30D (dry) | 0.379 |
| | Triethyl citrate | 1.517 |
| | Cabosil | 0.379 |
| Step 3. Seal coat | Opadry Clear (Hydroxypropylmethyl cellulose) | 1.899 |
| | Cabosil | 0.271 |
| Total | | 70.0 |

Process:
1. Dissolve oxycodone HC 1 and Opadry (HPMC) in water. Spray the drug solution onto non-pareil beads in a fluid bed coater with Wurster insert.
2. Disperse Eudragit RS, Eudragit RL, triethyl citrate, and Cabosil in water. Spray the dispersion onto the beads in the fluid bed coater.
3. Dissolve Opadry in water. Spray the solution onto the beads in the fluid bed coater.
4. Cure the beads at 60° C. for 24 hours.

One or more aversive agents as described herein can be incorporated into a capsule with the oxycodone beads, into the oxycodone beads, or on the oxycodone beads by one skilled in the art. The one or more aversive agents may be in releasable, non-releasable, or substantially non-releasable form or a combination thereof. Preferably, when beads comprising the aversive agent(s) are incorporated into the capsule they are indistinguishable from the oxycodone beads.

Example 16

Controlled Release Hydromorphone

A sustained release hydromorphone HCl formulation is prepared having the formula in Table 16 below:

TABLE 16

| Ingredients | Amt/unit (mg) |
|---|---|
| Hydromorphone HCI | 12.0 |
| Eudragit RSPO | 76.5 |
| Ethocel | 4.5 |
| Stearic acid | 27.0 |
| Total | 120.0 |

Process:
1. Blend milled Stearic acid, ethocel, Hydrocodone Bitartrate, and Eudragit RSPO using a V-blender.
2. Extrude the mixture using a Powder Feeder, Melt Extruder (equipped with the 6×1 mm die head), Conveyor, Lasermike, and Pelletizer.
   Powder feed rate—4.2 kg/hr; vacuum—~980 mBar
   Conveyor—such that diameter of extrudate is 1 mm
   Pelletizer—such that pellets are cut to 1 mm in length
3. Screen pellets using #16 mesh and #20 mesh screens. Collect material that passes through the #16 mesh screen and is retained on the #20 mesh screen.
4. Fill size #2 clear gelatin capsules with the pellets. Range: NLT 114 mg and NMT 126 mg.

One or more aversive agents as described herein can be incorporated into a capsule with the hydromorphone pellets, into the hydromorphone pellets, or on the hydromorphone pellets by one skilled in the art. The one or more aversive agents may be in releasable, non-releasable, or substantially non-releasable form or a combination thereof. Preferably, when pellets comprising the aversive agent(s) are incorporated into the capsule they are indistinguishable from the hydromorphone pellets.

Example 17-20

Examples 9-12 can be repeated utilizing a sufficient amount of capsaicin in place of, or in addition to the aversive agents disclosed therein.

While the invention has been described and illustrated with reference to certain preferred embodiments thereof, those skilled in the art will appreciate that obvious modifications can be made herein without departing from the spirit and scope of the invention. Such variations are contemplated to be within the scope of the appended claims.

What is claimed is:

1. An immediate release oral dosage form comprising:
   a compressed mixture, comprising:
      a therapeutically effective amount of oxycodone hydrochloride;
      a gelling agent comprising polyethylene oxide, the polyethylene oxide in a ratio to oxycodone hydrochloride from about 1:1 to about 8:1 by weight;
      a disintegrant;
      sodium lauryl sulfate; and
      magnesium stearate,
   the dosage form providing an immediate release of the oxycodone hydrochloride when orally administered to a human patient.

2. The immediate release oral dosage form of claim 1, wherein the ratio of the polyethylene oxide to the oxycodone hydrochloride is from about 2:1 to about 8:1.

3. The immediate release oral dosage form of claim 1, wherein the gelling agent is in an effective amount to form a gel when the dosage form is subjected to tampering by dissolution in about 0.5 ml to about 10 ml of an aqueous liquid.

4. The immediate release oral dosage form of claim 3, wherein the aqueous liquid is water.

5. The immediate release oral dosage form of claim 3, wherein the gel has a viscosity of at least 10 cP.

6. The immediate release oral dosage form of claim 3, wherein the gel has a viscosity of at least 60 cP.

7. The immediate release oral dosage form of claim 1, further comprising an additional drug selected from the group consisting of an NSAID, a COX-2 inhibitor, acetaminophen, aspirin, an NMDA receptor antanalgesic, a drug that blocks a major intracellular consequence of NMDA-receptor activation, an antitussive, an expectorant, a decongestant, an antihistamine and mixtures thereof.

8. The immediate release oral dosage form of claim 1, wherein the ratio of the polyethylene oxide to the oxycodone hydrochloride is from about 1:1 to about 3:1.

9. The immediate release oral dosage form of claim 1, further comprising microcrystalline cellulose.

10. The immediate release oral dosage form of claim 1, further comprising silicon dioxide.

11. The immediate release oral dosage form of claim 1, wherein the dosage form is a tablet.

12. The immediate release oral dosage form of claim 1, wherein the gelling agent is in an effective amount to impart a viscosity of at least 120 cP when the dosage form is subjected to tampering by dissolution in from about 0.5 to about 10 ml of an aqueous liquid.

13. The immediate release oral dosage form of claim 1, wherein the gelling agent is in an effective amount to impart a viscosity from about 120 cP to about 5,000 cP when the dosage form is subjected to tampering by dissolution in from about 0.5 to about 10 ml of an aqueous liquid.

14. The immediate release oral dosage form of claim 3, wherein the imparted viscosity makes the tampered dosage form difficult to pull into an insulin syringe.

15. The immediate release oral dosage form of claim 3, wherein the imparted viscosity makes the tampered dosage form difficult to pull into an insulin syringe as compared to the same dosage form having an inert pharmaceutically acceptable excipient in place of the gelling agent.

16. The immediate release oral dosage form of claim 3, wherein the tampered dosage form cannot be filled into an insulin syringe without picking up pockets of air.

17. The immediate release oral dosage form of claim 3, wherein the tampered dosage form has a milk like color.

18. The immediate release oral dosage form of claim 3, wherein the viscosity is imparted when the dosage form is subjected to tampering by crushing and dissolution in the aqueous liquid.

19. The immediate release oral dosage form of claim 3, wherein the viscosity is imparted when the dosage form is subjected to tampering by dissolution in the aqueous liquid at ambient temperature.

20. The immediate release oral dosage form of claim 3, wherein the viscosity is imparted when the dosage form is subjected to tampering by dissolution in the aqueous liquid with heating greater than 45° C.

21. The immediate release oral dosage form of claim 1, wherein the polyethylene oxide has a weight average molecular weight from about 100,000 daltons to about 1,000,000 daltons.

22. The immediate release oral dosage form of claim 1, wherein the polyethylene oxide has a weight average molecular weight from about 1,000,000 daltons to about 10,000,000 daltons.

23. The immediate release oral dosage form of claim 1, comprising about 2.5 mg to about 10 mg of the oxycodone hydrochloride.

24. The immediate release oral dosage form of claim 1, comprising about 5 mg of the oxycodone hydrochloride.

* * * * *